US011957512B2

(12) United States Patent
Baumann

(10) Patent No.: US 11,957,512 B2
(45) Date of Patent: Apr. 16, 2024

(54) PRESSURE MEASUREMENT DEVICE FOR MEASURING PRESSURE AND/OR FOR MEASURING ELASTICITY OF A VEIN OR AN ORGAN AND FOR COMBINATION WITH AN ULTRASOUND MEASUREMENT UNIT, PRESSURE MEASUREMENT SYSTEM, AND METHOD

(71) Applicant: VeinPress GmbH, Muri B. Berm (CH)

(72) Inventor: Ulrich A. Baumann, Münsingen (CH)

(73) Assignee: Compremium AG, Muri B. Bern (CH)

( * ) Notice: Subject to any disclaimer, the term of this patent is extended or adjusted under 35 U.S.C. 154(b) by 757 days.

(21) Appl. No.: 16/885,799

(22) Filed: May 28, 2020

(65) Prior Publication Data
US 2020/0315583 A1    Oct. 8, 2020

Related U.S. Application Data

(63) Continuation-in-part of application No. PCT/IB2018/059354, filed on Nov. 27, 2018.

(30) Foreign Application Priority Data

Nov. 28, 2017 (DE) .................... 10 2017 221 330.2

(51) Int. Cl.
*A61B 8/00* (2006.01)
*A61B 5/03* (2006.01)
*A61B 8/08* (2006.01)

(52) U.S. Cl.
CPC ................ *A61B 8/429* (2013.01); *A61B 5/03* (2013.01); *A61B 8/4281* (2013.01); *A61B 8/485* (2013.01);
(Continued)

(58) Field of Classification Search
CPC ......... A61B 8/429; A61B 5/03; A61B 8/4281; A61B 8/485; A61B 2562/0247;
(Continued)

(56) References Cited

U.S. PATENT DOCUMENTS

| 5,394,877 A | 3/1995 | Orr et al. |
| 5,759,162 A | 6/1998 | Oppelt et al. |

(Continued)

FOREIGN PATENT DOCUMENTS

| CH | 707 046 A2 | 3/2014 | |
| CH | 707046 A2 * | 3/2014 | ............... A61B 8/04 |

(Continued)

OTHER PUBLICATIONS

Machine Translation of WO-2011030415, Patent Translate, pp. 1-30, printed on Mar. 24, 2023 (Year: 2011).*

(Continued)

*Primary Examiner* — Yi-Shan Yang
*Assistant Examiner* — Om Patel
(74) *Attorney, Agent, or Firm* — Finch & Maloney PLLC

(57) ABSTRACT

A pressure measurement device for measuring pressure and/or for measuring elasticity of a vein, an organ or a compartment of a body in combination with an ultrasound measurement unit. A pressure sensor is configured as a thin film pressure sensor with the speciality that the intermediate space, between the films of the film pressure sensor, is filled with an ultrasound-transparent and electrolytically/electrically inactive liquid. The films of the film pressure sensor are fabricated from an ultrasound-transparent material.

17 Claims, 8 Drawing Sheets

Figure 1:
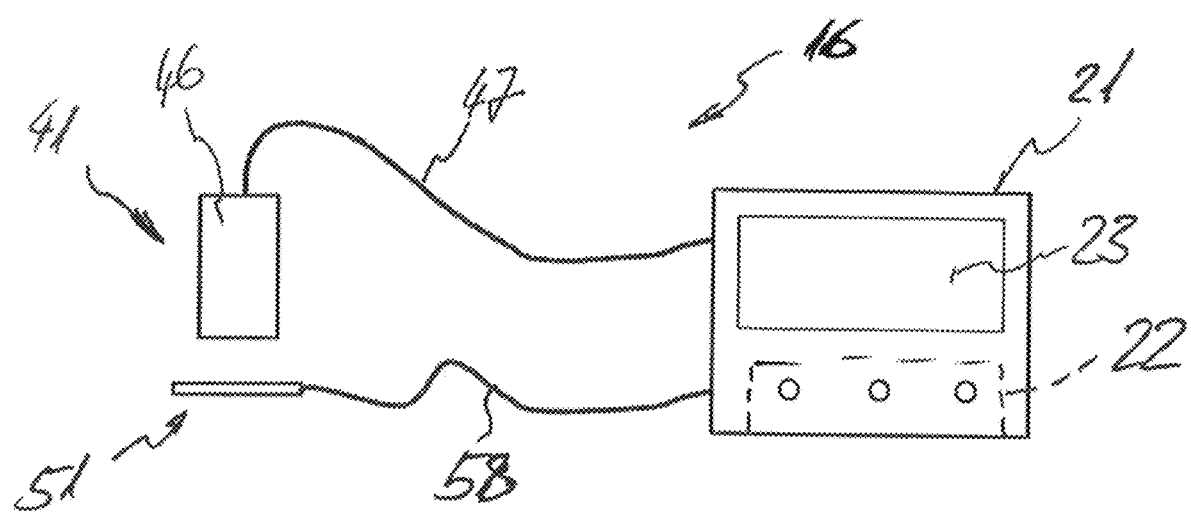

(52) U.S. Cl.
CPC ... *A61B 2562/0247* (2013.01); *A61B 2562/12* (2013.01)

(58) Field of Classification Search
CPC .......... A61B 2562/12; A61B 2562/168; A61B 5/022; A61B 5/0053; A61B 8/4272; A61B 8/04; A61B 8/4416; A61B 8/56
See application file for complete search history.

(56) References Cited

U.S. PATENT DOCUMENTS

| | | |
|---|---|---|
| 2007/0270720 A1 | 11/2007 | Fry |
| 2010/0036243 A1* | 2/2010 | Matsumura .............. A61B 8/12 600/443 |
| 2016/0089110 A1* | 3/2016 | Milkowski ........... A61B 8/4281 600/472 |

FOREIGN PATENT DOCUMENTS

| | | | |
|---|---|---|---|
| CN | 1134659 | * | 10/1996 |
| DE | 42 07 463 A1 | | 9/1993 |
| DE | 10 2015 116 383 A1 | | 3/2016 |
| EP | 0 120 410 A2 | | 10/1984 |
| EP | 0 920 833 A1 | | 6/1999 |
| EP | 1 415 596 A1 | | 5/2004 |
| WO | WO-0182779 A2 | * | 11/2001 .......... A61B 5/0053 |
| WO | WO-2011030415 A1 | * | 3/2011 ......... A61B 5/02035 |

OTHER PUBLICATIONS

Machine Translation of CN-1134659, Patent Translate, pp. 1-19, printed on Mar. 27, 2023 (Year: 1996).*
Peng Y, Shkel YM, Hall TJ, A Tactile Sensor for Ultrasound Imaging Systems, IEEE Sens J. Feb. 15, 2016;16(4):1044-1053, printed on Dec. 8, 2023, https://www.ncbi.nlm.nih.gov/pmc/articles/PMC4751986/ (Year: 2016).*
Machine Translation of CH-707046-A2, Patent Translate, pp. 1-16, printed on Dec. 11, 2023 (Year: 2014).*
https://www.interlinkelectronics.com/standard-products dated May 17, 2020, See Spec., p. 13.
https://www.interlinkelectronics.com/force-sensing-resistor dated May 17, 2020, See Spec., p. 13.
Marshall-Goebel et al., "Assessment of Jugular Venous Blood Flow Stasis and Thrombosis During Spaceflight", JAMA Network Open, Nov. 13, 2019, pp. 1-11, See Spec., p. 19.
Baumann et al., "Estiamtion of Central Venous Pressure by Ultrasound", Resuscitation, Elsevier, IE, Bd. 64, Nr. 2, Feb. 1, 2005, pp. 193-199, See International Search.
German Search Report Corresponding to 10 2017 221 330.2 dated Aug. 2, 2018.
International Search Report Corresponding to PCT/IB2018/059354 dated Mar. 27, 2019.

* cited by examiner

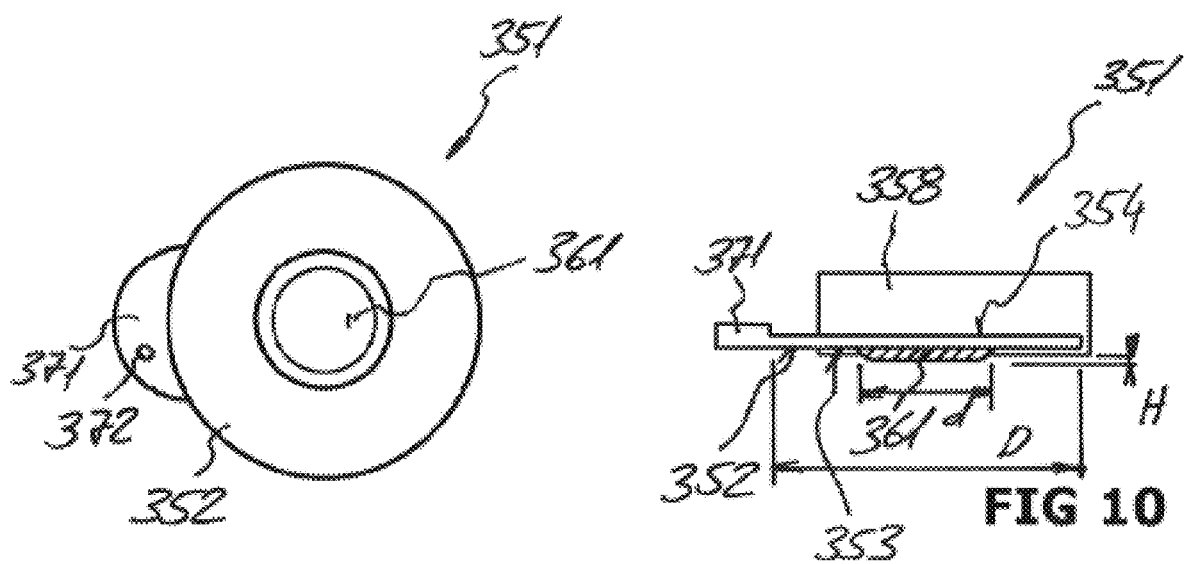
FIG 9
FIG 10
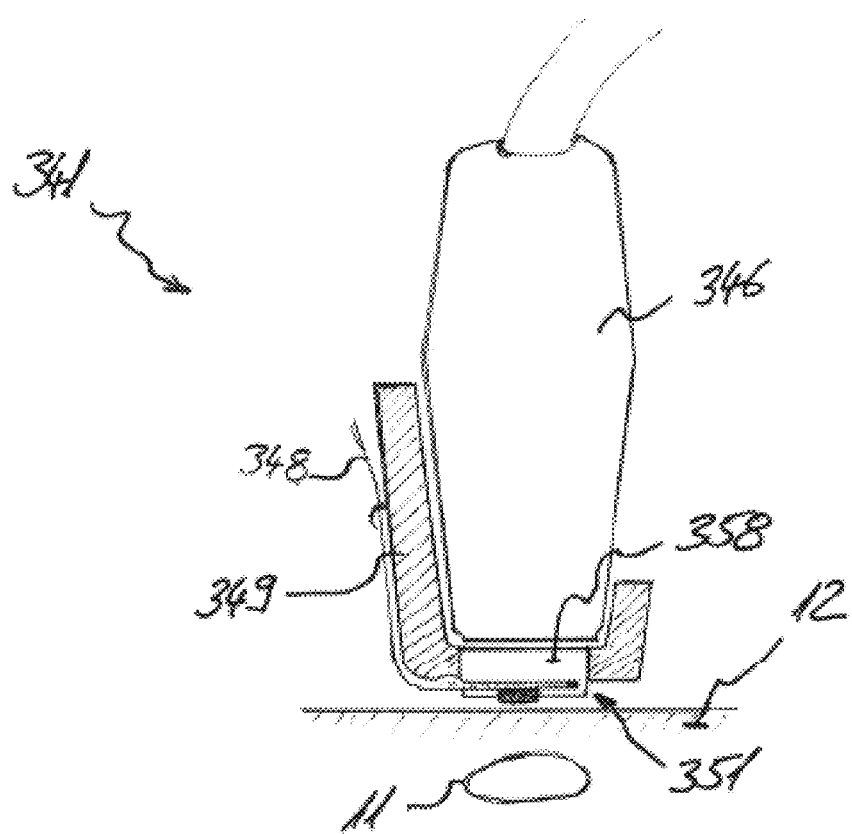
FIG 8

PRESSURE MEASUREMENT DEVICE FOR MEASURING PRESSURE AND/OR FOR MEASURING ELASTICITY OF A VEIN OR AN ORGAN AND FOR COMBINATION WITH AN ULTRASOUND MEASUREMENT UNIT, PRESSURE MEASUREMENT SYSTEM, AND METHOD

The invention relates to a pressure measurement device according to the preamble of the claims and a pressure measurement device according to the preamble of the claims, as well as a pressure measurement system for measuring pressure and/or measuring elasticity of veins, organs or compartments as claimed and a measurement device for measuring pressure and/or measuring elasticity of a vein, an organ or a compartment as claimed, as well as a method for measuring pressure and/or measuring elasticity of a vein, an organs or a compartment according to the claims.

The invention also relates to further new methods for measuring pressure of select organs or compartments according to the claims.

The pressure or elasticity in the tissue of a living organism is to be measured, wherein, simultaneously, the tissue is observed by means of ultrasound and methods which evaluate its reflection at the tissue.

The term "compartment" is understood in this context as an anatomically defined space which can be delimited with respect to the surroundings. In addition to muscle compartments, for example, the abdomen and the skull are also compartments. Since these new types of measurements are attributed to the inventor, Dr Ulrich Baumann, they are designated as "Pressure measurements according to Baumann".

In general, ultrasound investigations using commercially available ultrasound measurement units, in particular, transducers and imaging methods, are known from everyday medical investigation.

In this case, ultrasound is emitted into the tissue from the transducer, reflected there and the transit time differences are processed by imaging methods to form an image of the interior of the tissue to be studied. Here, the application of pressure to the transducer to characterize pressure-induced tissue and vascular changes is well-established.

In particular, this is used in the compression of veins for the diagnosis of thrombosis. In the case of this investigation method, however, the pressure applied by means of the transducer depends on the experience of the operator of the transducer and differs from investigator to investigator. In connection with the display of vascular structures and body fluids moving therein, in particular, Doppler methods are used to determine the flow rate, which methods necessitate fitting additional equipment to commercial ultrasound devices.

From EP 1 415 596 A1, a pressure measurement device is known for ultrasound measurement devices which substantially consists of a rigid container.

A stiff membrane is inlaid on a flat side which is used for coupling to the ultrasound measurement head. A flexible contact membrane is attached to the opposite flat side which terminates the interior formed by the housing.

The interior of the pressure measurement device is filled with an ultrasound-transparent liquid. The pressure present in the interior can be determined via a line by means of an external apparatus.

A disadvantage of the known solution is that this pressure measurement device is advantageously used as a disposable product to ensure hygiene requirements, but has manufacturing costs which do not justify merely a single usage of the same on an economic level.

From CH 707 046 B1, a further pressure measurement device is known for measuring pressure of a vein or an organ and for combination with an ultrasound measurement unit which has proved very successful in practice. However, also in the case of this pressure measurement device, the manufacturing costs lie in a range which economically do not justify merely a single usage of the same.

DE102015116383A1 discloses a small box-shaped component (40), which, according to the description in Paragraph 0034, is a tensiometer or an ultrasound sensor for measuring distance or a pressure transducer which is arranged in a bubble. It does not follow comprehensibly from this document how precisely the measurement is made using this small component (4), on the other hand, this structure shows that a pressure measurement of an interposed pressure measurement sensor functions in connection with a transducer (30).

Although this structure comprises a film, it does not come under the concept of a film pressure sensor as used by the present patent application.

According to the invention, a film pressure sensor is namely a pressure measurement sensor which has two opposite films, which have an electrically active coating in the interior, which coatings, when they come in contact with one another, give a characteristic value for the applied pressure via resistance measurement. This type of pressure sensor is tried and tested and can be easily manufactured industrially.

They can, however, fundamentally not be used in combination with ultrasound-imaging methods since in the intermediate space where the electrically active coatings are located, they contain air which acts like a barrier layer with respect to ultrasound. The present invention recognizes that such known sensors would be desirable as a result of their flatness and good functional capability but must be modified since they are not usable per se.

US2007/0270720A1 from 2007 shows a similar principle to that already presented by the inventor in 2004 where a compressible cushion is also arranged between a transducer and a patient, whose internal pressure is measured by means of an external pressure gauge.

It is therefore the object of the present invention to provide a new type of, and advantageously improved pressure measurement device, a pressure measurement system, a measurement device and methods for measuring pressure and/or measuring elasticity of veins, organs or compartments which can be produced more cost-effectively than previous solutions and can be operated simply and reliably.

A solution which could be used economically meaningfully as a single-use article for hygiene reasons would be particularly desirable.

The object is achieved for a pressure measurement device and a pressure measurement system as well as for a measurement device and a solution for a method for measuring pressure and/or measuring elasticity of a vein, an organ or a compartment as claimed. The patent claims further protect special pressure measurement methods according to Baumann.

Furthermore, a new type of pressure sensor is to be provided which can be optimally used for these applications. Likewise new measurement methods are to be provided with the aid of which it is easier for the physician to make a diagnosis.

Finally, a new type of use is protected for a film pressure sensor.

According to the invention, a pressure sensor configured as a film pressure sensor is provided, wherein an intermediate space between the films of the film pressure sensor is filled with an ultrasound-transparent and electrolytically (electrically) inactive liquid (the liquid is an electrical isolator and/or does not conduct electrical current).

Film pressure sensors of the relevant type, e.g. a force sensing resistor (FSR) made by Interlinks Electronics, have a sandwich structure with two films. The first film is electrically coated or printed on the inner side. The other film has an electrical contact grid on the inner side which is applied by means of printing or coating. The two films are held at a distance from one another by a spacer and direct contact of the coated and/or printed film sections is prevented. The spacer is formed in such a manner that a hollow intermediate space filled with ambient air is formed (conventional). The distance of the films from one another is designed according to the object and can be kept very small which enables a flat embodiment of the film pressure sensor. The technical expression film pressure sensor therefore also originates from this since the pressure sensor has a film character (it is as flat as a film). When pressure is applied to the film pressure sensor, the coated and/or printed sides of the films come in contact and form electrical bridges depending on the applied pressure. The measurable electrical resistance thereby changes, and the magnitude of the applied pressure can be determined by means of the same.

When measuring the elasticity of a vein, an organ or a compartment, an elasticity quotient is determined and correlates with a venous pressure, an organ pressure or a compartment pressure.

According to the invention, the intermediate space of such a conventional film pressure sensor is filled with an ultrasound-transparent electrolytically/electrically inactive liquid so that the ambient air is completely removed from the intermediate space. As a result, a commercial film pressure sensor becomes ultrasound-transparent and thus the pressure sensor according to the invention. As a result, a reliable pressure measurement can be ensured at low costs of the pressure measurement device.

This results in a new type of use of conventional film pressure sensors namely for pressure measurement of veins, vessels or compartments according to Baumann in the interior of closed elastic objects, human or animal bodies.

In one embodiment of the invention, the intermediate space is filled with the ultrasound-transparent and electrolytically inactive liquid during manufacture of the film pressure sensor.

Alternatively the filling takes place after manufacture of the film pressure sensor by repetitive compression in immersion or vacuum. Another possibility is a direct injection of the ultrasound-transparent and electrolytically inactive liquid into the intermediate space shortly before use.

Preferably, the films of the film pressure sensor are fabricated from an ultrasound-transparent material, at least in some regions with the result that the ultrasound transparency of the film pressure sensor is further improved.

Preferably the ultrasound-transparent and electrolytically inactive liquid is a liquid from the group of aqueous (nonconducting) liquids, ultrasound-transparent gels, synthetic oils, or biological oils which ensure a good ultrasound transparency of the film pressure sensor. Biological oils have proved particularly preferable. For example olive oil or rape seed oil. However also synthetic oils designated as food oil can be used substantially when they consist of food-safe synthetical oils. An example for such an oil is: Blaser Swisslube Foodoil SH 22, Item 00700-01 or Blaser Swisslube Foodoil SH32, Item 00701-01.

Preferably at least one pressure transmission element is provided, which ensures a precise pressure measurement even on elastic supports such as are the skin or the tissue. In the case of elastic supports, a flattening of the pressure behaviour curve can be established which does not correspond to the effective pressure behaviour. This is brought about, for example, by a suction phenomenon between the spacer edges and the elastic support. By means of the at least one pressure transmission element, such a suction phenomenon can be avoided, and better pressure transmission can be ensured.

The at least one pressure transmission element is advantageously fabricated from an ultrasound-transparent material, with the result that the at least one pressure transmission element does not influence the ultrasound measurement or only to a limited extent. Being furthermore advantageous, the at least one pressure transmission element is fabricated from the same material as the film with the result that no influences caused by material differences occur when measuring the pressure and/or measuring the elasticity of the vein or the organ. Being particularly advantageous, the at least one pressure transmission element is formed with or on the film with the result that the influence of the pressure transmission element on the pressure measurement and/or the elasticity measurement of the vein, the organ or the compartment is additionally reduced.

Preferably, the at least one pressure transmission element is arranged on an outer side of the film pressure sensor or the pressure measurement device which can be brought to abut with the ultrasound measurement unit, with the result that an optimal pressure transmission through the ultrasound measurement unit is ensured.

Advantageously, the at least one pressure transmission element has a height extension which at least corresponds to the spacing of the films of the film pressure sensor from one another (e.g. 0.2 mm) with the result that an optimal pressure transmission through the ultrasound measurement unit is ensured.

A height extension which corresponds to 5 times to 20 times the spacing of the films of the film pressure sensor from one another has proved particularly advantageous for optimal pressure transmission in experiments.

Further advantageously the at least one pressure transmission element has an extension which approximately corresponds to 30% to 70% of the corresponding extension of the intermediate space of the film pressure sensor with the result that an optimal pressure transmission through the ultrasound measurement unit is ensured.

In experiments an extension of the at least one pressure transmission element which corresponds to approximately 40% to 60% of the corresponding extension of the intermediate space of the film pressure sensor has proved successful for an advantageous pressure transmission.

In an alternative to this, the at least one pressure transmission element is preferably arranged on an outer side of the film pressure sensor or the pressure measurement device which can be brought to abut with the skin or the tissue, with the result that an optimal pressure transmission via the pressure measurement device through the ultrasound measurement unit is ensured.

Alternatively a complete overlap (100%) of the film pressure sensor is also possible.

In a special embodiment, at least the side of the film pressure sensor facing the transducer is constructed with a raised film so that a separate pressure transmission element is omitted but the effect of a pressure transmission element is certainly achieved. It is obvious to configure the relevant film accordingly so that on the one hand, the raising has the same effect as in the pressure transmission element but, on the other hand, the electrical properties of the interior coating of the same film are sufficient for the resistance-based pressure measurement.

In a further alternative embodiment, respectively one pressure transmission element is arranged both on the outer side which can be brought to abut with the ultrasound measurement unit, as well as on the outer side of the film pressure sensor or the pressure measurement device which can be brought to abut with the skin or the tissue, with the result that the advantages of the one arrangement of the pressure transmission element can be combined with the advantages of the other arrangement of the pressure transmission element.

Preferably a reservoir is provided for the ultrasound-transparent and electrolytically inactive liquid wherein a liquid connection is provided between the reservoir and the intermediate space of the film pressure sensor. The usability and the storage capability of the pressure measurement device is thus increased substantially since the ultrasound-transparent and electrolytically inactive liquid can escape, evaporate or thicken. For measurement reasons an opening to the intermediate space of the film pressure sensor is advantageous and should not be closed. Advantageously, the film pressure sensor is arranged in the reservoir with the result that a compact embodiment of the film pressure sensor is made possible and a simple exchange of the ultrasound-transparent and electrolytically inactive liquid between the film pressure sensor and the reservoir is ensured.

An oblong channel can be provided as a particular embodiment of the reservoir which is formed in a laterally projecting element of the film pressure sensor. For comparison we observe FIGS. 3 to 5, where an opening can be seen for the escape of liquid from the intermediate space, but no oblong channel is provided.

Figure 11:
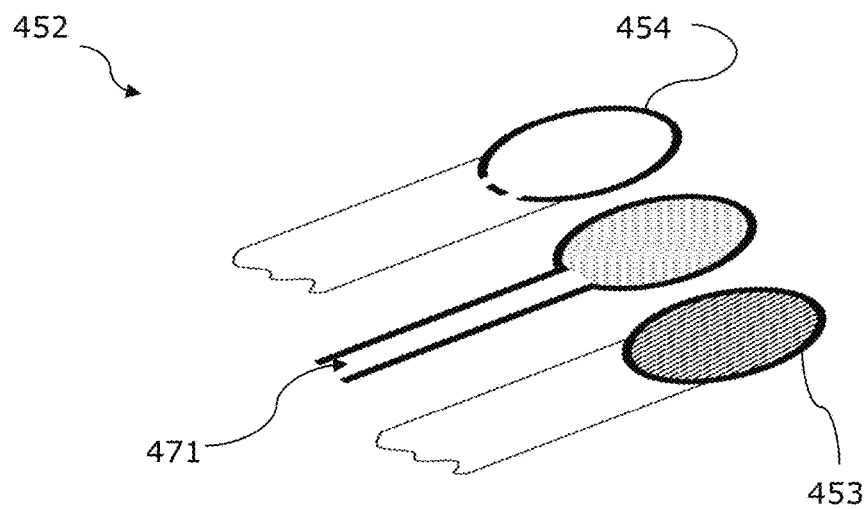

FIG. 11, on the other hand, shows such an oblong channel. The channel according to the invention is used, on the one hand, for filling the intermediate space with the liquid and therefore also for removal of air from the intermediate space, on the other hand, it permits an escape of liquid from the intermediate space. The size of the channel is dimensioned in such a way that, in the case of a full load on the pressure sensor, all the liquid escaping from the intermediate space finds space. That is, if the intermediate space is not pressure-loaded, the channel is almost empty or only slightly filled. The channel therefore allows a to-and-fro flow of the liquid depending on the pressure loading of the film pressure sensor without the liquid escaping into the surroundings and without the air entering into the intermediate space. In order to ensure this, the liquid is selected to be of such condition that its cohesion property and adhesion property is adapted to the geometric formation of the channel. The channel can be closed for the storage and transport state of the film pressure sensor. In this case, the closure is only opened when using the film pressure sensor. For certain applications, the channel can also be permanently closed at its outlet so that the liquid can flow to and fro against an air column in the channel. This structure has the disadvantage however that at different ambient air pressure the film pressure sensor measures different pressure values which can be taken into account in a precise measurement evaluation by compensation.

In order that the intermediate space/channel interplay takes place optimally, the dimensioning of the intermediate space and the channel and the cohesion properties of the liquid are designed so that the liquid basically remains in the intermediate space and only goes from there into the intermediate channel when the intermediate space is compressed as a result of the action of pressure and then flows back into the intermediate space. In this respect, it is optionally advantageous if the liquid is equipped in such a manner that its cohesion forces are higher than its adhesion forces.

Preferably a data line, e.g. a connecting cable, is provided for relaying the values determined by the film pressure sensor, with the result that these values can be transmitted simply to an evaluation device.

Alternatively a transmitter is provided for relaying the values determined by the film pressure sensor, wherein these values can be transmitted simply to an evaluation device without a data line restricting the handling of the pressure measurement device. A radio connection is preferred as the transmission standard, for example a Bluetooth® or Zigbee® connection.

Preferably, a holding device is provided for the pressure measurement device with the result that the pressure measurement device can be fixed if required and enables an improved measurement.

Advantageously, the holding device is configured in such a manner that this can be temporarily fixed on a tissue. For example, the holding device comprises adhesive surfaces, at least in some regions, similar to a plaster which adhere to the tissue. In one alternative to this the holding device comprises holding strips which can be placed around a body part or body section and fixed, e.g. by means of Velcro closures.

Preferably, the film pressure sensor is embedded in an ultrasound-transparent embedding material, at least in some regions, with the result that the pressure measurement device according to the invention has a certain stiffness and ensures a longer usability.

Preferably the embedding material is an ultrasound-transparent silicone, which can be easily processed.

A particular embodiment is obtained if this silicone is elastically deformable and has a Shore hardness of about 30.

A further embodiment of the embedding material e.g. silicone-elastomer is obtained if this also has self-adhesive properties so that pressure measurement device can, for example, be stuck to the skin and/or can be stuck detachably to the transducer by means of the embedding material. It could be e.g. a material from Siltec GmbH & CO KG from Weiler im Allgäu/Gwermany named SilSoft® 103-200-0L0 and it could have a density of about 0.99 g/cm3 ISO2811. Preferably it is free of peroxide and/or corresponds ISO 10993 USP Class VI.

Preferably it is suitable for steam sterilization.

The adhesive properties of the silicone-elastomer are preferably such that it has a higher cohesion than adhesion. That is it can be removed non-destructively from the skin and/or from the transducer.

Advantageously, the embedding of the film pressure sensor is provided on the outer side of the film pressure sensor which can be brought to abut with the skin or the tissue, with the result that a sufficient stiffness of the pressure measurement device is given for most applications of the pressure measurement device according to the invention.

In an alternative embodiment, the film pressure sensor is completely embedded in the embedding material with the result that a component which can easily be used in handling is provided, which can also be integrated constructively simply in devices.

For the case of the elastic embedding material with adhesive property, there is also the advantage that the transducer does not slip with respect to the place to be investigated during the measurement and simultaneously, the embedding material reliably transmits the ultrasound without additional gel.

A pressure measurement system according to the invention for measuring pressure and/or measuring elasticity of a vein or an organ comprises a pressure measurement device according to the invention with at least one of the aforesaid features and an ultrasound measurement unit wherein the pressure measurement device and the ultrasound measurement unit are coupled to one another to form a measurement unit. This pressure measurement system is easily transportable and can be configured compactly.

Advantageously the pressure measurement device and the ultrasound measurement unit can be coupled mechanically to a mechanical measurement unit which enables a simple connection of the two components (click system). Advantageously the mechanical coupling can be configured to be detachable with the result that the pressure measurement device in particular can easily be exchanged if required.

In one variant, the pressure measurement device and the ultrasound measurement unit are connected to form a measurement unit.

A measurement device according to the invention for measuring pressure and/or measuring elasticity of a vein, an organ or a compartment has at least one processing unit and a pressure measurement system which comprises an ultrasound measurement unit and a previously described pressure measurement device.

The measurement device has a combination of the aforesaid advantages in handling. As a result of the easy operability, the training time of the operating staff is reduced whilst ensuring a safe application.

In a further embodiment of the pressure measurement system according to the invention, the pressure and/or the elasticity of a collapsing vein or the degree of deformation of an organ or a compartment can be determined in a particularly advantageous manner. An organ or a compartment need not be completely imaged in the ultrasound for the pressure measurement and/or elasticity measurement since the pressure measurement and/or elasticity measurement can also be made only on one organ part or on one section or portion of a compartment ("compartment window") whilst ensuring reproducible and reliable measurement results. This applies in particular when the portion investigated is representative of the remaining organ. As a result, even large organs such as, for example, a liver or a muscle compartment can be measured.

In a further embodiment of the pressure measurement system according to the invention, the point in time of collapse of the vein can be determined particularly advantageously automatically, for example by computer evaluation of the ultrasound measurement results combined with the pressure measurement values.

In a further embodiment of the pressure measurement system according to the invention, the point in time of vein collapse can be determined particularly advantageously by image-processing and/or image-evaluating methods which analyse ultrasound images.

In a method for measuring pressure and/or measuring elasticity of a vein, of an organ or a compartment according to the invention, a pressure and/or an elasticity can be determined particularly advantageously using a pressure measurement device according to the invention, whereby in a partially automated manner the combined ultrasound measurement unit and pressure measurement device is pressed onto a tissue until it is identified by means of a signal evaluation that a vein is collapsed or a certain degree of deformation of an organ or compartment is achieved and the corresponding pressure in the film pressure sensor is measured.

Preferably a software is provided and used for carrying out the image-processing method. Such software is an independent invention for itself. The collapsed state of the vein is identified in this case by conversion of raw data (pixels) into a cross-sectional area of the vein through which flow takes place. An arbitrary reduction in cross-section compared with the cross-section of the unloaded vein can be defined as the criterion for collapse. In the case of organs the degree of deformation of the organ or the organ part is determined accordingly by the displacement of tissue-induced pixel abnormalities (e.g. blood vessels, density differences etc.). As has already been explained, for a pressure measurement and/or elasticity measurement of an organ using the pressure measurement device according to the invention, this need not be completely imaged in the ultrasound.

In an advantageous further embodiment of the software, the automatic identification of the beginning of the measurement cycle is defined by the beginning of the deformation of the vein or by the beginning of the reduction in the cross-sectional area through which flow takes place. In the case of organs or organ parts, the point in time at which the pixel abnormalities begin to shift is advantageously selected.

In a further advantageous further embodiment of the software, the automatic identification of the measurement quality is defined by determining the position of the observed vein or the organ or the organ part with respect to the measurement axis of the ultrasound measurement head or ultrasound transducer and/or the film pressure sensor of the pressure measurement device. Advantageously account is also taken of the position of the vein or the organ with respect to neighbouring and, in particular, underlying structures such as bones or the like.

In an advantageous further embodiment of the software an automatic decision is made relating to acceptable or unacceptable measurement by taking into account and analysing all the aforesaid data.

The inventions described above will be presented hereinafter once again and predefined with further improvements as well as with the mentioned new measurement methods.

In the following summary, individual points are assumed to be known from the medical viewpoint or only mentioned in keywords. These can be supplemented by the author at any time.

INTRODUCTION

The use of non-invasive ultrasound-assisted pressure measurement using a VeinPress device (which in principle permits a pressure measurement according to Baumann) is well documented scientifically in over 20 publications in medical journals and several presentations. These measurements have been carried out so far using the VeinPress2014 pressure gauge. This known pressure gauge has been replaced in the present invention by a thin new type of film pressure gauge (film pressure sensor).

The prior art is presented hereinafter with its advantages and disadvantages as well as the object of the invention and its solution using a new film pressure sensor according to the invention.

The following objects can be solved at the present time with the improved new development; pressure measurements in:

Acute and chronic compartment syndrome

Non-invasive intracranial pressure measurement in newborns via the fontanelle

Non-invasive intracranial pressure measurement in children and adults

Non-invasive measurement of the ocular pressure through the eyelid

Non-invasive measurement of the venous pressure and the central venous pressure

Measurement of the pressure in the internal jugular vein in space medicine

Prior Art

In all previously known comparable pressure measurement systems a liquid-filled bubble in front of an ultrasound head is described to measure the contact pressure of the ultrasound head on the tissue. The pressure sensor/pressure transducer must be attached outside the sound cone since this is non-transparent to ultrasound waves due to its construction and would interfere with the imaging. Depending on the construction the sensor is attached laterally in the bubble itself or with this via a connection. This arrangement necessitates a zero calibration before each measurement. This also applies to the VeinPress system 2014. These technical solutions are expensive and for reasons of hygiene or transmission of germs they are not very suitable for clinical use, in particular they are too expensive for single use.

Advantages of the Prior Art

The formation by means of a "bubble" is advantageous for pressure transmission. Thus, for example, in the pressure measurement in a vein, a soft liquid-filled cavity (bubble) is directed against the likewise liquid-filled vein (blood) with the result that pressures during compression match and nevertheless can be readily measured (Laplace law). In addition, the fixing of a bubble with connected pressure gauge before the transducer (VeinPress device from 2014) gives the investigator the freedom to make a measurement at the location of current interest. Furthermore, all previous scientific works have been carried out using this system so that good experience with this prior Art measuring device is already available.

Disadvantages of the Prior Art

Mention should be made of the high item costs and the difficult to solve problem of hygiene and/or transmission of infection from one patient to another. The system must also be calibrated before each measurement (to zero) which makes it difficult to compare the measurement results and to objectivize them. During longer use wear effects at the membranes and loss of liquid occur so that incorrect measurements can occur. Thus, relatively high maintenance costs are incurred.

Object of the Invention

The object is to develop a pressure measurement system for single use (hygiene/item costs) which in particular prevents the aforementioned disadvantages of zero calibration, maintenance costs and therefore possible incorrect measurements due to wear and has no or very low maintenance costs and has a friendly design in application for the investigator and for the patient.

Solution of the Object

In order to solve the object a pressure sensor configured as a film pressure sensor is provided wherein the intermediate space between the films is filled with an electrolytically/electrically inactive ultrasound-transparent liquid. Thus, a conventional film pressure sensor per se is itself configured to be transparent for ultrasound waves. Zero calibrations are omitted since these film pressure sensors can be produced mechanically of the same type and are correspondingly precise.

Due to the single use, problems of infection transmission are omitted. Consequently there is also no damage due to wear and no expensive maintenance costs. The new film pressure gauge according to the invention can be stuck onto the tissue to be investigated as a plaster solution or attached directly in front of the ultrasound head by means of a holder. In addition, an adhesive solution is also now possible, preferably by means of an ultrasound-transparent silicone-elastomer, which has adhesion properties, which allow the pressure sensor to be detachably bonded in a non-destructive manner to the skin and/or to the ultrasound head (transducer) by means of which a connection is established, where, on the one hand, no ultrasound gel is necessary and, on the other hand, a reliably non-slip connection from the area to be examined to the transducer is given.

The non-destructive detachability is achieved by the fact that the silicone-elastomer has a higher cohesion than adhesion. This means that the cohesion forces are greater than the adhesion forces (adhesive forces), although the adhesion forces are relatively high (good adhesive force).

Film Pressure Sensors

Conventional film pressure sensors of the relevant type, such as a force sensing resistor made by Interlinks Electronics, have a sandwich design with two films; see: (https://www.interlinkelectronics.com/standard-products dated 17 May 2020) and there in particular: (https://www.interlinkelectronics.com/force-sensing-resistor dated 17 May 2020;

The first film is electrically coated or printed on the inner side. The opposite film has an electrical contact grid on the inner side, which was also applied by means of printing or coating. The air-filled intermediate space is formed by a lateral spacer. Commercially available film pressure gauges have a thickness of 0.5 mm. When pressure is applied to the sensor (on the films of the sensor), the two printed or coated films come into contact and form electrical bridges depending on the pressure applied. The measurable electrical resistance changes depending on the pressure applied. The contact surface of the electrically actively coated films coming into contact is defined as an "electrically active surface". During compression, the air in the intermediate space between must be able to escape or be compressed. For this purpose, one or a plurality of openings (ventilation channels) are provided preferably as gaps in the spacer.

The pressure sensor described here so far is not suitable for ultrasound waves produced by commercially available ultrasound devices in diagnostic use. Said devices are operating at frequencies between 2-20 megahertz. This is because the air in the intermediate space of said pressure sensors is not only electrically an insulator, but also largely absorbs and/or reflects ultrasound waves at such frequencies and does not let them through. Behind the pressure gauge, there is subsequently a so-called "sound attenuation" for a user, as is described in ultrasound literature, e.g. for gallstones. As a result, such sensors cannot be used without the step according to the invention and up until this point, such conventional sensors are generally ruled out in the context of ultrasound diagnostics.

The core point of the invention and new is that, instead of air, the intermediate space of said pressure sensors is filled with a liquid that is ultrasound-transparent and is not electrically active (non-conductive). This makes a conventionally constructed film pressure sensor for ultrasound-transparent and simultaneously ensures insulation between the electrically active film sheets in a pressure-free state.

According to the invention, this is the first and only solution where a conventional film pressure sensor as such is made ultrasound-transparent for ultrasound investigations. This is the ingenious idea of converting a conventional film pressure sensor by filling the intermediate space between the films with a special liquid.

Figure 2:
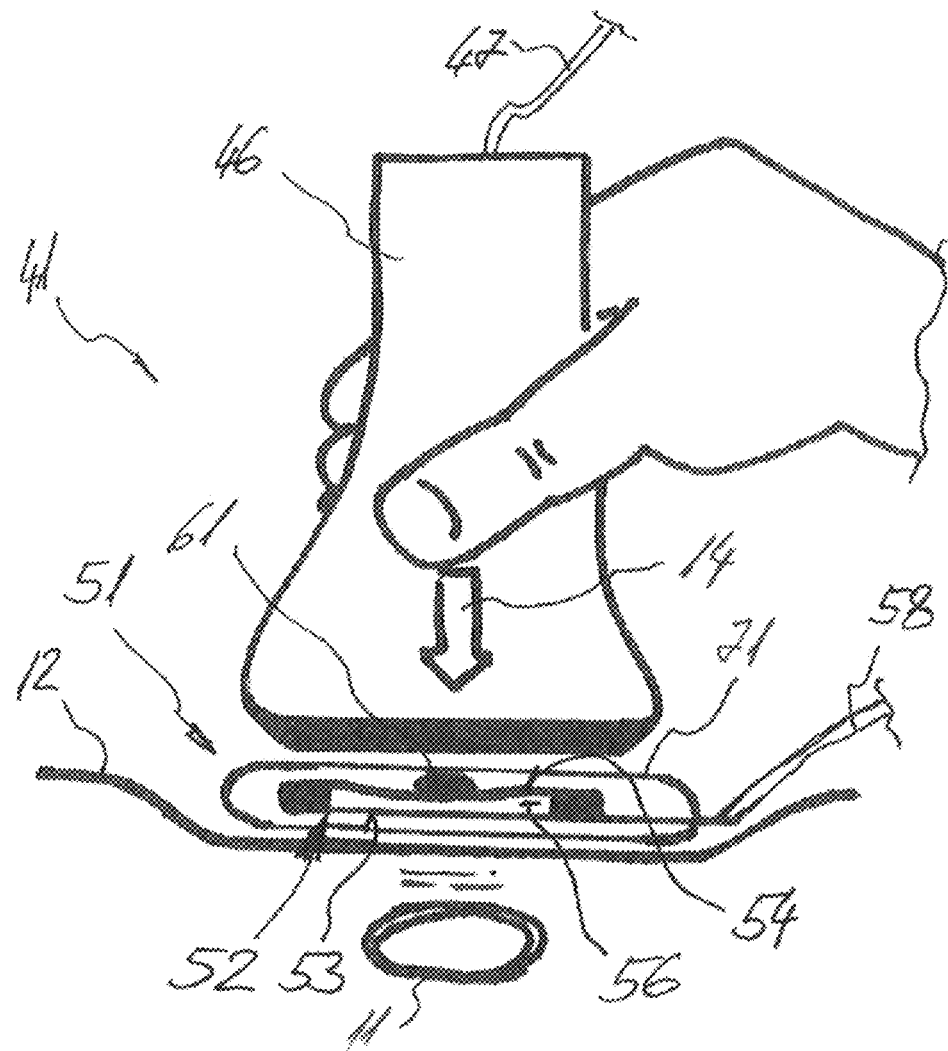

Advantages of Ultrasound-Transparent Film Pressure Sensor According to the Invention Film pressure sensors are thin (e.g. 0.5 mm) and can be produced in shape and size according to the intended task. Commercially manufactured sensors are partly produced in large quantities and are correspondingly cost-effective. They can be deformed without compromising the measurement results (bending up to 90 degrees). They are suitable according to the invention in a revised embodiment for the pressure measurement in the context of an ultrasound examination. The use can be done as a plaster at the place of interest on the skin/tissue, which can be important, for example, for a follow-up check (repetitive measurements at the same point in the patient) ("plaster solution"). Another type of use of the pressure gauges is a fixed connection with the ultrasound head ("click solution"), which is preferably used for diagnostics with a single measurement; as an alternative to the click solution, the film pressure sensor could also be glued to the transducer by means of a plaster solution. The investigator is thus free to carry out a new pressure and ultrasound measurement during an examination at the site of interest. Due to the low cost, the sensors can be designed for single use. This eliminates hygiene problems. Zero calibration is no longer necessary due to the precise manufacturing possibilities for such film pressure sensors. These film pressure sensors can therefore also do without an enveloping reservoir, as is illustrated in FIG. 2.

Figure 12A:
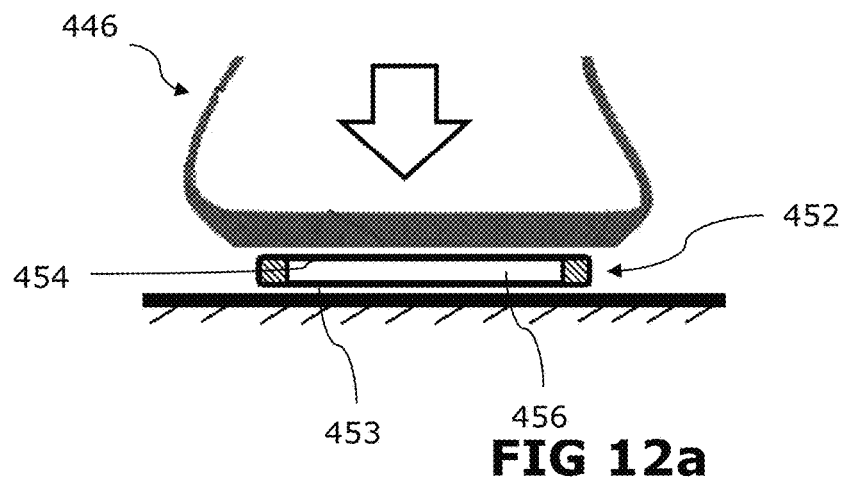
Figure 12B:
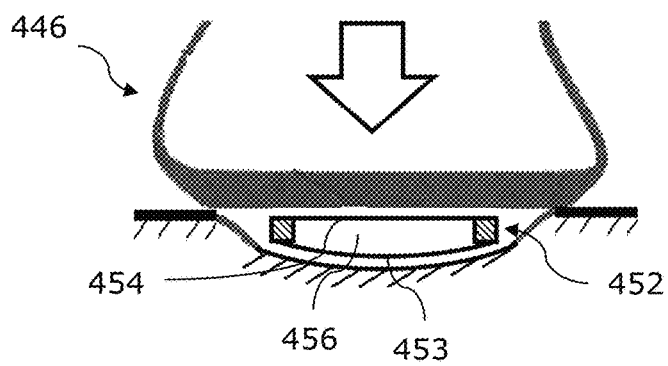

Limitations and Further Improvements of the Inventive Ultrasonic-Transparent Film Pressure Sensors and Solution of the Same General Information:
a. The limitations result from the typical design of the film pressure gauges. The two electrically active film surfaces facing each other must be connected and/or compressed by the applied pressure. They are separated from each other by a spacer. If the applied pressure is not in the centre of the film but on this—often ring-shaped—spacer, no measurement is possible. This occurs when the underlay is hard and the usually linear ultrasound head rests on the spacer (see FIG. 12a). Even when the ultrasound head tilts sideways, it can come into contact with the spacer, which can lead to incorrect measurements. With an elastic underlay—as the human skin represents—a vacuum phenomenon can be observed with increasing pressure (FIG. 12b).

The film pressure sensor as a whole is held pressed into the elastic underlay, wherein the spacer still supports against the underlay as before the pressure of the transducer. Transducers with a smaller diameter than the diameter of the spacer or new pressure transmission elements offer a remedy. This can be easily recognized from FIGS. 12a and 12b.

Figure 13A:
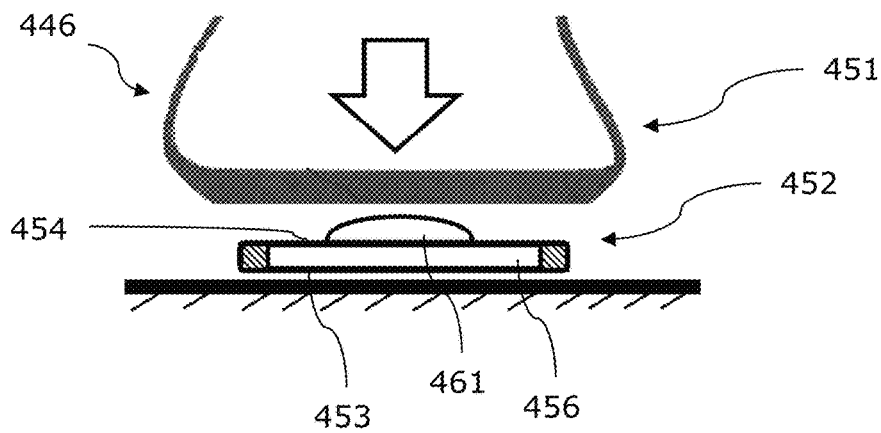
Figure 13B:
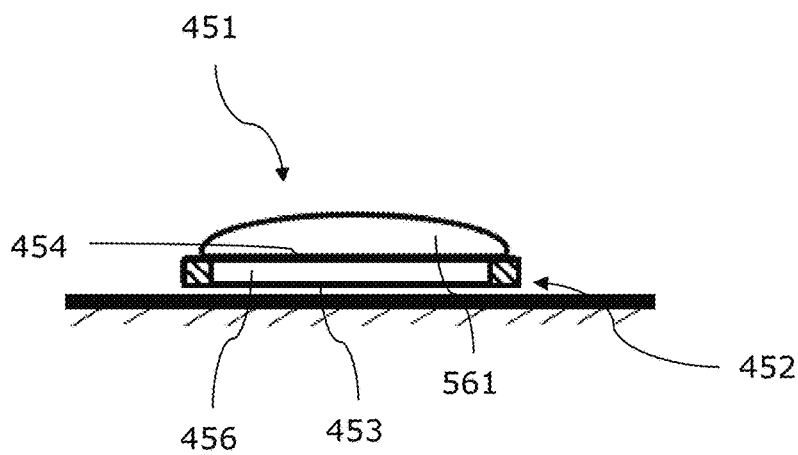
Figure 13C:
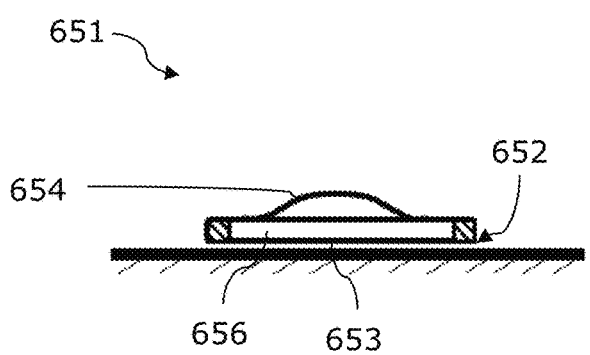
Figure 13D:
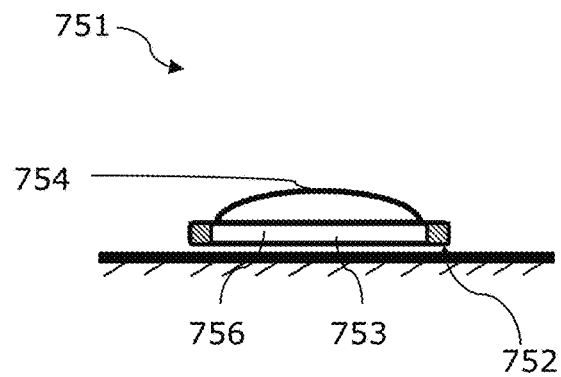

Spacer/Pressure Transmission Element as an Alternative Improvement Element
a. The limitations are dissolved by the introduction of a spacer on the outside of the film of the film pressure sensor. This is applied or formed on the externally on the film pressure gauge on one or both sides in such a way that the electrically active surfaces come into contact with pressure on the pressure transmission element and can be pressed together. The spacers can thus be formed according to FIGS. 13a to 13d.
b. FIG. 13a shows a film pressure sensor 452, on whose upper film 554 a semi-lens-shaped spacer 461 is placed approximately in the centre.
c. FIG. 13b shows a comparable structure, wherein the mounted spacer has a larger diameter and covers the entire film pressure sensor. In this case, the spacer assumes a type of bubble function by proficiently transferring a pressure exerted from above onto the film pressure sensor due to elastic properties of this semi-lens-shaped bubble. We make it clear to the person skilled in the art that there is room between these two superstructures depending on the requirements of the variants. The structure according to FIG. 13c deviates from that in that not a spacer is placed on the upper film, but in which the film 654 itself is cambered. This is also the analogue structure according to FIG. 13d, only with a wider formation of the upper film 754.
d. The pressure transmission element used according to the invention to improve conventional film pressure sensors can be rigid or elastic, but must consist of ultrasound-transparent material, e.g. made of silicone or silicone-elastomer. If necessary, self-adhesive silicone-elastomer, which is also easily removable, is also used.
e. Properties and Formation of the Pressure Transmission Element ("Height Extension"):
f. Thickness: The distance between the films is approx. 0.2 mm (commercially available FSR 402 made by Interlins Electronics). It is preferable to require the height of the pressure transmission element to also be at least 0.2 mm. In addition, the spacer should not rest on the side of the spacer when the ultrasound head is slightly tilted by the investigator. Investigations have shown that the thickness of the pressure transmission element should optimally have 5-20 times the intermediate space between the pressure gauge, meaning 1-4 mm for example.
g. Extension: When the pressure transmission element is formed in a point shape (pin head), the film sensor reacts already to the smallest pressures, but then shows a flat increase in pressure (only a small electrically active surface is formed). A half-lens shape has proven to be universally applicable. It can have a smaller diameter than the ring-shaped spacer of the film pressure sensor (e.g. FIG. 13a) or, in the case of sufficient elasticity, it can also cover the entire film pressure sensor (e.g. FIG. 13n). Optimum pressure transmissions take place with an extension of the pressure transmission element of 30-70% of the electrically activatable surface and/or diameter with round formation of the film sensor.

h. Formation and Hardness: Advantageously, the pressure transmission element is rounded on one side (half-lens or ring-cake shape) with an ultrasonic-transparent material that is as soft as possible (e.g. silicone Shore hardness 30).

i. Precision: The film pressure sensors ("force sensing resistors") are indicated in literature as rather inaccurate pressure gauges. In-house measurements show that e.g. the FSR 402 long made by Interlins Electronics, has a spread of <3% in the pressure measurement range relevant for our use between 5-100 mBar (=5-100 cm $H_2O$), which allows absolutely sufficiently precise measurements from a medical point of view.

Filling of the Sensor According to the Invention a. Requirements for the Liquid: The liquid is intended to replace the insulator air in the intermediate space, i.e. that it is not electrolytically/electrically active and secondly, is transparent for ultrasound. A biological oil or a synthetic foodoil made by Blaser Swisslube SH22 (00700-01) or Swisslube SH32 (00701-01) is preferred (after many experiments).

b. Filling: The intermediate space between the sensors is filled during the production of the sensor by means of a vacuum or needle injection via an expansion opening.

c. Reservoir/Dehydration: When the film pressure gauge is compressed, the space between the films is reduced and the liquid there must be able to spread. This is done via openings made on the side of the spacer. A kind of reservoir must be provided here (e.g. by a lateral covering). This is also intended to prevent leakage.

d. The preferred embodiment of a film pressure sensor according to the invention results in a construction with extended electrical connection lines. A film pressure sensor is meant by this, the electrical connections of which and the spacer of which project relatively long and parallel on the side. The intermediate space between the film pressure sensor is laterally extended in a channel-shaped manner in such a way. On the one hand, this channel serves to fill the cavity with oil (the above mentioned biological or synthetic oil) and on the other hand, it is not completely filled with oil (the electrolytically/electrically inactive liquid) itself. Due to the capillary effect of the channel (adhesion) and the cohesion of the oil, an expansion space for the oil is created between the end of the oil-filled area and the outlet of the channel, which is pressed towards the outlet of the channel, depending on the compression of the intermediate space of the film pressure sensor, or runs back into the intermediate space.

e. FIG. 11. shows an extended spacer area/channel 471 in conjunction with the intermediate space.

f. Producing such a channel 471 is relatively easy in that the upper 454 and the lower film 453 of the film pressure sensor is simply also extended to this lateral projection and completely covers it. Likewise, the spacer between the two films is also extended towards the lateral projection (thick line in the middle image of FIG. 11) so that the channel 471 is thereby formed.

g. FIG. 11 thus shows a technical possibility to extend the intermediate space via channel 471 and thus prevent the liquid from leaking out of the intermediate space and from the film pressure sensor.

Sterility: Single use. In the case of a plaster solution (see above), the sensor is inserted on or between two plasters as commonly used in the field of medicine. These are sterile at least on the sides coming into contact with patient. Sensors made by Interlink FSR 402 can be sterilized with hydrogen peroxide for example without loss of function.

Figure 14A:
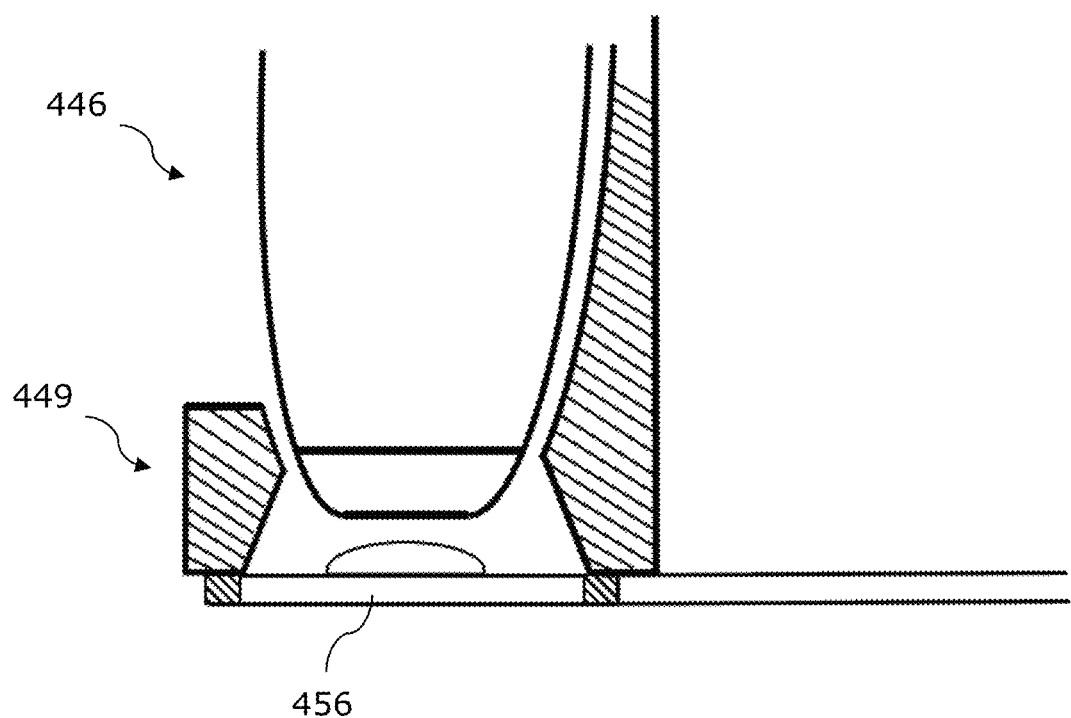
Figure 14B:
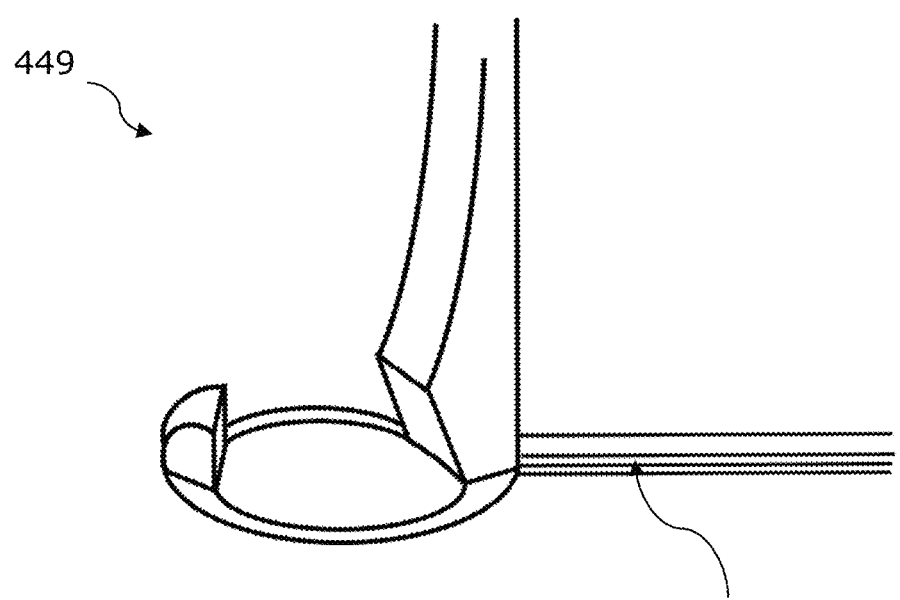
Figure 14C:
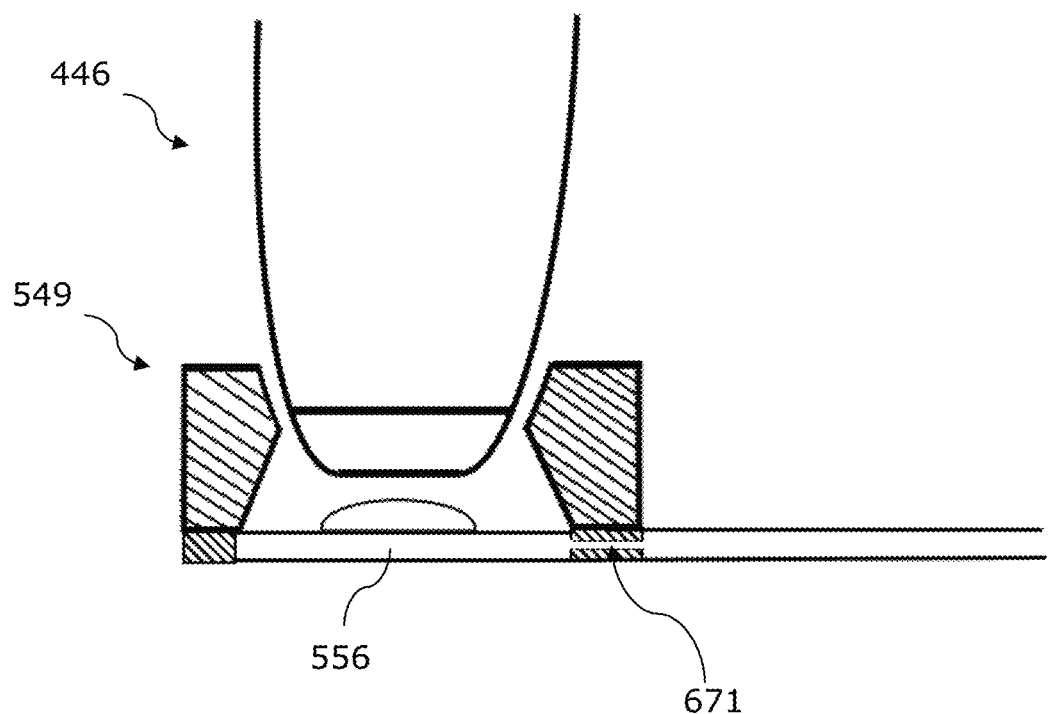
Figure 14D:
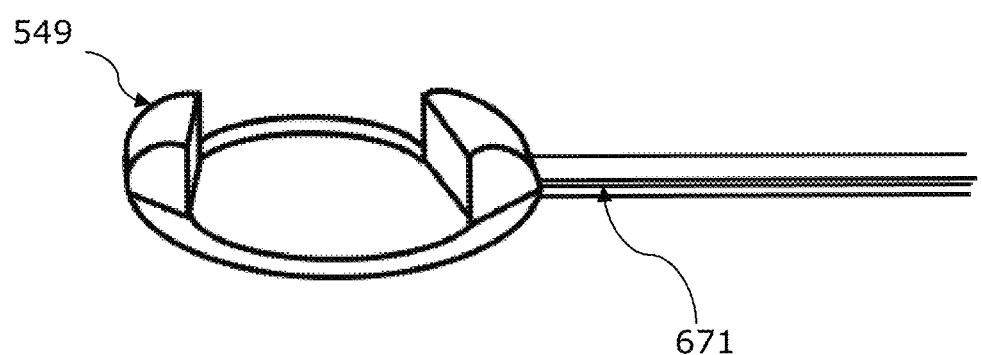

Ultrasound Head Coupling Guidance System: A kind of haptic guide rail/target device/gauge is provided, which conducts the transducer on the pressure sensor and prevents unconscious faulty measurements. The guide rail has at least the width of the ultrasound head and can also be made of non-ultrasound-transparent material.

a. FIG. 14a, FIG. 14b FIG. 14c and FIG. 14d show different embodiments of lateral guidance systems. In particular, the structure according to FIGS. 14c and 14d is also used as a guide for "targeting" the site to be observed and for attaching the transducer. On the other hand, an investigator can also efficiently position and align with the target area with the aid of the guidance system, even in the case of dimmed lighting, as is often desired during ultrasound investigations.

Conversion and Transmission of Measurement Data

Figure 6:
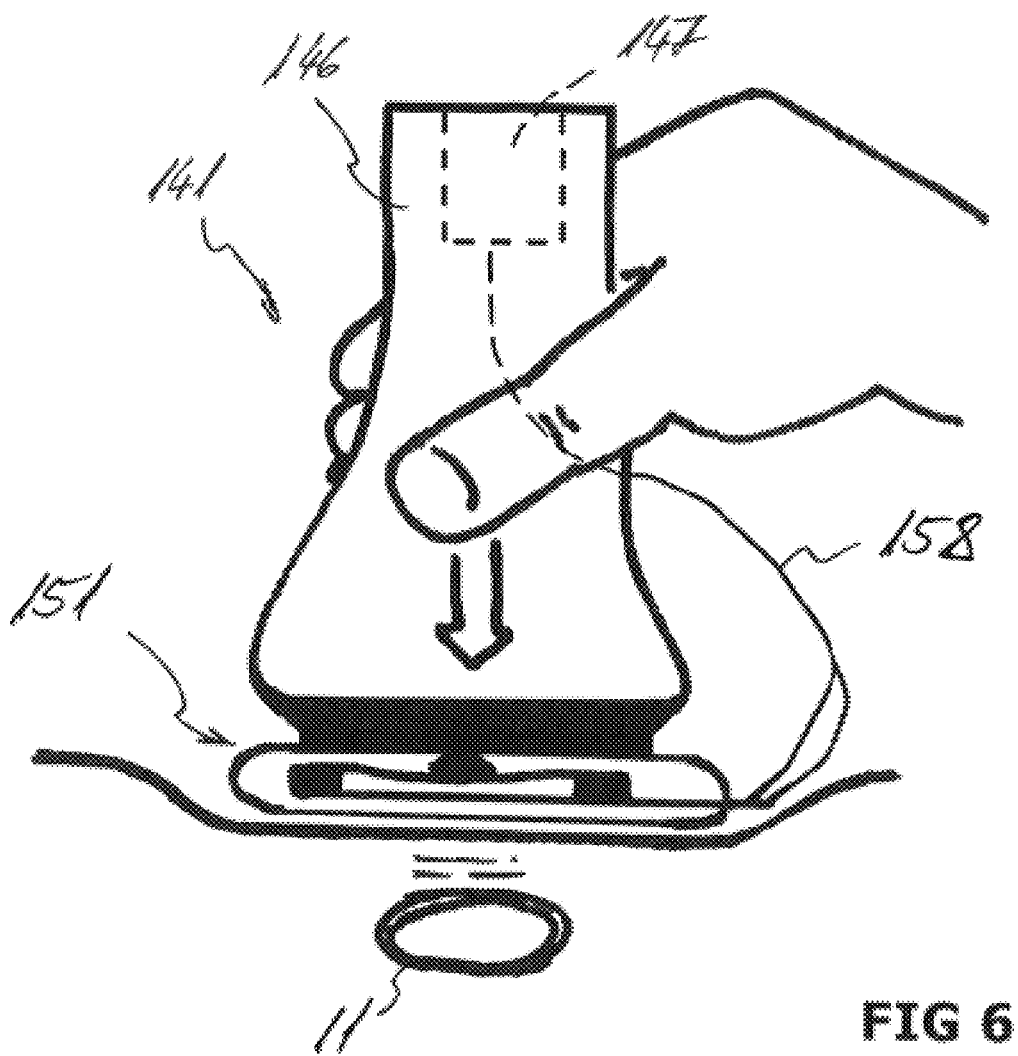

Described using an embodiment of FIG. 6 for example:

Definition of Different Measuring Locations on the Patient According to Indications Compartment Syndrome: Basically, the pressure disperses evenly in a muscle compartment. This means that we can select the optimal compression location for an ultrasound examination to make a measurement. Best results are achieved if a muscle compartment can be compressed against the bone and the pressure can be applied vertically onto the skin:

a. Tibialis anterior compartment: 2-5 cm lateral of the anterior tibia edge, middle third, structure of the onset of the Interosseous ligament at the posterior tibia edge (method according to Dr R. Sellei).

b. Deep tibialis posterior compartment: Examination of dorsal when the knee is bent, e.g. kneeling on the surface of the chair, compression via aponeurosis of the soleus muscle from the middle to lower third.

Intracranial Pressure in New-Borns: The pressure gauge is applied to the open fontanelle. The distance from the skin to the skull base is suitable as distance measurement.

Non-Invasive Intracranial Pressure Measurement in Children and Adults: The internal jugular vein has a direct access to the base of the skull in the compartment of the skull interior. To measure intracranial pressure, the patient's head is placed in a slight low position (head down tilt) and the internal jugular vein is interrupted by finger pressure from the outside in the caudal section. This creates a kind of riser tube for inside the skull. The pressure in the intracranial segment of the internal jugular vein can then be measured as with usual vein compressions. In addition, it is possible to measure the flow in the internal jugular vein (so-called doppler or duplex ultrasound examination). The blood in this vein usually flows to the heart. By slowly tilting the bed with the head end down, this flow comes to a standstill when the pressure from the skull is identical to the retroactive pressure from the heart. This moment of pressure/flow equalization corresponds to the pressure inside the skull in such a way that the pressure in the internal jugular vein is to be regarded as a surrogate for the intracranial pressure. The pressure measurement according to Baumann is then carried out by compression of the internal jugular vein.

Non-Invasive Measurement of the Ocular Pressure: The examination is carried out via the closed eyelid, e.g. on the side of the cornea. The examination can also be carried out intra-operatively, in this case preferably laterally to the vitreous body.

Non-Invasive Measurement of Venous Pressure and Central Venous Pressure: see various publications by Dr Ulrich A. Baumann.

Pressure Measurement in Internal Jugular Vein e.g. for Space Purposes: see NASA publications, in particular publication dated 13 Nov. 2019, Jama Network, available at: https://jamanetwork.com/journals/jamanetworkopen/fullarticle/275 5307.
  a. (Here, the VeinPress system from 2014 was used for the above measurements without the film pressure sensor of the invention)

Non-Invasive Measurement of Acute Compartment Syndrome According to Baumann

Status of Current Diagnostics
  a. To ensure the diagnosis of "acute compartment syndrome", the compartment is currently dotted with a needle and the pressure in the compartment is measured via an artificially injected liquid cushion. The needle is blindly inserted into the muscle compartment through the skin. As a result, failed punctures are possible. The puncture pain leads to a reflective increase in muscle tension, which can lead to incorrect high measurement values. Puncture is invasive, associated with the risk of bleeding or infection. It can only be carried out by a doctor with sufficient anatomical knowledge. Repetitive measurements for an assessment of progression are hardly carried out due to the disadvantages mentioned above.

Advantages of the Non-Invasive, Ultrasonic-Associated Determination of the Compartment Pressure by Means of the Invention
  a. The procedure is non-invasive and painless, which is particularly beneficial in paediatrics. The investigator first obtains an overview of the compartment by means of ultrasound and can then select the optimal measuring point. Due to the single use of the measuring sensor according to the invention, hygiene is provided for; there are no skin injuries. The measurements can be carried out by non-medical personnel after a short training. Repetitive and comparative measurements are possible during the course of repetitive and comparative measurements in such a way that the method is particularly suitable where it is probable that a pressure increase develops in a compartment, such as after reperfusion interventions due to acute ischemia of the lower extremity.
  b. It is also not possible with the invention to directly measure the pressure inside a compartment in a non-invasive manner. The measuring principle according to the invention is based on the fact that an increase in pressure in a compartment leads to a hardening of the tissue, respectively to a decrease in elasticity. The elasticity measurement is carried out according to the invention by measuring the contact pressure of the ultrasound head on the skin and this contact pressure is combined with the decrease in the diameter of the compartment when pressing in (pressure measurement according to Baumann), which can be detected in the ultrasound image. By combining pressure and distance, the elasticity of the tissue can be determined, for example by the representation of an elasticity curve and/or its gradient or measurement at predefined pressure. Best results are achieved when the logs are compressed against a bone and a clearly visible measuring point is set in the ultrasound image (e.g. area of the bone).

Limitations of Non-Invasive Pressure Measurement by Means of the Pressure Measurement Sensor According to the Invention
  a. Imaging ultrasound measurement devices are standard in most clinics. The staff can easily be trained in the application of pressure measurement and ultrasonic anatomy. This does not necessarily require medical training.

Preferred Measurement Process According to the Invention
  a. The doctor examines the compartment with conventional ultrasound and marks the measuring point on the skin. The ultrasound (US)-contact gel is cleanly removed.
  b. The pressure sensor according to the invention is removed from its sterile packaging, whereby it activates. This means that, on the one hand, the electrical contacts are exposed, and, on the other hand, the channels are opened for oil expansion so that they can communicate pneumatically with the ambient air. In addition, the adhesive surface is cleared.
  c. The sensor is placed on the measuring point and slightly pressed. Due to the coating of the pressure sensor with self-adhesive silicone-elastomer, no gel is required for sound transmission according to the invention. The sensor adheres to the skin, but can also be removed from it without residue.
  d. The transducer is applied to the pressure gauge. The adhesive silicone-elastomer creates a tight connection so that the ultrasound head cannot slip during the exertion of pressure. On the other hand, the adhesive forces of the silicone-elastomer are selected in such a way that it can also be separated from the transducer without residue (see above).
  e. Now the measurement is carried out by the investigator by increasing the pressure on the ultrasound head and measuring the distance change caused by it in the compartment.
  f. The pressure readings of the sensor are transmitted optically and/or acoustically to the investigator.
  g. The evaluation of the measurement can be carried out on the one hand by an evaluation of the elasticity curve (gradient) or by measuring the distance when a pre-defined pressure value is reached. Advantageously, the value is represented in % of the outlet diameter. Initial results in patients with compartment syndrome show that a normal relaxed muscle can be squeezed by 20% with a compression of 80 mBar. If this value falls below 10%, a compartment syndrome is likely present and, under 5%, it is certainly present.
  h. Points 4.2-4.7 can be carried out by non-medical staff.
  i. The doctor can check the measurement at any time or perform a follow-up measurement.
  j. At the end, the doctor issues the diagnosis based on the measurement values of the pressure and the imaging.
  k. In summary, the invention allows the detection of measurement values on the tissue elasticity by means of ultrasound imaging with simultaneous compression pressure measurement.

Non-Invasive Measurement of Chronic Compartment Syndrome (Chronic Compartment Syndrome) According to Baumann Status of Current Diagnostics
  a. The chronic compartment syndrome of the lower leg occurs under stress, for example, in joggers. It is characterized by pain that occurs during the stress and which forces the athlete to take a break or to stop altogether. As with acute compartment syndrome, the current diagnosis is carried out by means of needle puncture of the corresponding compartment before and immediately after strain (see also acute compartment syndrome, section 1). The deep dorsal lower leg compartment is most often affected. A pressure increase above 30 mmHg in the compartment is considered to be diagnostic.

Benefits of Non-invasive Ultrasound-Assisted Determination of Compartment Pressure
  a. They correspond to those for acute compartment syndrome.

Limitations of Non-Invasive Pressure Measurement
  a. The same arguments as in acute compartment syndrome.

Measurement Process
  a. Same procedure as for acute lodge syndrome.
  b. The deep flexor compartment is advantageously performed dorsally (from behind) with the lower leg at an angle laid astride on a chair.

Non-Invasive Measurement of Intracranial Pressure in New-Borns According to Baumann Current State of Intracranial Pressure Measurement in New-Borns ("Intracranial Pressure")
  a. A direct measurement of the intracranial pressure is only possible via a probe inserted into the brain, which is done via a borehole through the calvaria. This very invasive procedure is also therefore only carried out in exceptional cases. At appropriate clinic, a protruding fontanelle is observed as an expression of an increased intracranial pressure, supplemented at most by the palpating finger of the doctor. In addition, an increased pressure is assessed indirectly by means of imaging (for example, by the width of the ventricles).

Advantages of a Non-Invasive Ultrasound Based on the Invention Measurement of Intracranial Pressure in New-Borns Via the Open Fontanelle
  a. The brain of the new-born can be represented with ultrasound via the still open fontanelle. The measurement of the depth of the fontanelle to the base of the skull is simple by means of ultrasound and the pressure measurement according to the invention during a compression is possible without difficulty.
  b. It is not possible to directly measure intracranial pressure in a non-invasive ultrasound-assisted manner. The measuring principle according to the invention is based on the fact that an increase in pressure in the skull leads to a decrease in the elasticity of the intracranial compartment. This decrease in elasticity can be measured according to the invention by measuring the depth between fontanelle and skull base in combination with the measurement of the contact pressure of the ultrasound head.

Measurement Process
  a. The pressure sensor is removed from the packaging, whereby it activates. (Compare the data of acute compartment syndrome)
  b. The sensor is placed on the fontanelle, which is possible due to the self-adhesive and for ultrasound-transparent silicone-elastomer without the use of a gel.
  c. The transducer is placed on the sensor and connects to the self-adhesive silicone-elastomer so that it cannot slip during the compression process. The use of a gel is no longer necessary. (see 4.4 above)
  d. The depth of the skull between the fontanelle and the base of the skull is now measured during a compression process via ultrasound imaging and correlated with the pressure applied to the fontanelle.
  e. An elasticity curve can be created from it. Simultaneously or alternatively, a single measurement is also made at pre-determined compression pressure on the pressure sensor or on the fontanelle to determine the respective distance.

Further Measurement Methods
  a. 4.1 With the aid of the pressure sensor according to the invention, however, other complementary long-term measurement methods are also following the measurement according to 3. Possible:
  b. 4.2 The pressure sensor fixed by adhesive force on the fontanelle is additionally fixed after removal of the sound microscope by means of adhesive tape in the position.
  c. 4.3 A certain reasonable (low) contact pressure is maintained.
  d. 4.4 The pressure sensor now provides a corresponding pressure measurement signal corresponding to the previously diagnosed internal intracranial pressure.
  e. 4.5 The subsequent ongoing pressure measurement now indicates a relative increase or decrease in internal intracranial pressure.
  f. 4.6 According to previously created measurement curves, these measurements of the pressure development can be used to trace the respective total internal intracranial pressure.
  g. 4.7 Of course, this pressure sensor arrangement also provides for making perpetual statements concerning the frequency of blood supply in the brain (pulse). In addition to the intracranial pressure in symbiosis, in this way, this pressure measurement structure also provides other vital information about toddlers in intensive care treatment.
  h. 4.8 The evaluation electronics also enable the delivery of alarm signals as required.

Limitations of the Measurement Method
  a. There are no reliable experience or pilot studies since this measurement technology according to the invention has not yet been investigated in vivo. The pressure to be exerted should not exceed the pressure exerted by a doctor the palpation he performs and should only be applied in the short term.

Non-Invasive Measurement of Intracranial Pressure in Children and Adults According to Baumann Status of Current Diagnostics
  a. The intracranial pressure in the adult can be reliably only carried out by means of a measuring probe inserted into the skull via a borehole. Several non-invasive methods have been proposed without successfully being able to replace the invasive measurement.

Advantages of a Non-Invasive Measurement of Intracranial Pressure by Means of the Device According to the Invention
  a. A reliable measurement or estimation of intracranial pressure by a non-invasive simple method would remedy all the disadvantages of the invasive probe. Anatomically, in addition to the central vein of the eye, only the jugular vein has a direct connection to the basal intracranial veins via the jugular foramen at the base of the skull.
  b. On the other hand, the pressure in the veins of the base of the skull corresponds to the intracranial pressure. This can be assumed at least in a back position. The internal jugular vein is a direct riser to these basal veins. Therefore, the internal pressure of the brain can be measured via this according to the invention.

Measurement process a. The pressure sensor is removed from the packaging, which activates it.

b. The internal jugular vein is represented by ultrasound and the sensor is glued to the skin without contact gel on the skin in the intracranial third of the vein. For this purpose, the pressure sensor is provided with an adhesive, ultrasound-transparent silicone-elastomer coating. (see 4.4. above)

c. Now we lower the head end of the bed as in the case of a tilting table ("head down tilt"). During this process, the flow in the vein is represented by conventional—for example colour-coded ultrasound. As soon as the flow comes to succumb to the heart, the pressure in the vein corresponds to the intracranial pressure. This vein is used as a kind of riser pipe into the pressure chamber (skull interior).

d. Measurement of the pressure in the internal jugular vein is now measured according to the invention via the pressure sensor. For this purpose, the ultrasound head is attached to the pressure sensor. The adhesive silicone-elastomer coating prevents slipping during the measuring process. The pressure on the jugular vein is increased by pressing the transducer under observation of its volume until it collapses. According to the Laplace law, the pressure now measured (produced) corresponds to the pressure in the vein, which, according to the rising pipe principle, corresponds to the intracranial pressure on the other hand.

e. For the first time, internal intracranial pressure can be measured reproducibly reliably and non-invasively.

Limitations of the Measurement Process a. By supporting the head appropriately, it must be avoided that the neck muscles tighten during head down tilt manoeuvres and distort the measurement. If necessary, by means of a finger-pressing to or laxative veins can be closed from the outside during the measuring process. Currently, there are scientific indications for the described measurement process, but no proven clinical data have yet been established.

Non-Invasive Measurement of the Ocular Pressure According to Baumann

Status of Current Diagnostics a. Two established methods are in the foreground. In both, the flattening of the curvature of the cornea (cornea) is measured at direct pressure on it. In tonometry according to Goldmann, a prism is applied to the cornea after local anaesthesia and in the contact-free technique the indentation of the cornea is measured, which is caused by a short-dosed air blasts. In both methods, the eye must be open. They are not suitable for measuring eye pressure during surgery on the eye.

Benefits of Non-Invasive Ultrasound-Assisted Measurement of Ocular Pressure a. The ultrasound measurement is carried out by the closed eyelid. Local anaesthesia is not necessary. It can be done from the front in the visual axis via the anterior eye chamber or sideways outside the cornea and here, directly measure the posterior portion of the eye and/or the pressure in the vitreous body. This lateral access is suitable for eye surgery performed via the anterior eye chamber. With single use of the pressure sensor, the hygiene problem can be easily solved.

b. It is not possible to directly determine the pressure in the eye (=intra-ocular pressure) non-invasively. The measuring principle is based on the measurement of the elasticity of the eye with light compression and simultaneous measurement of the eye diameter with ultrasound.

Measurement Process a. The doctor determines whether the measurement in the visual axis is carried out from the front or lateral to the vitreous body.

b. The pressure sensor is removed from the pack, which activates it (see above for details).

c. The pressure sensor is placed on the eyelid. It connects due to its coating with adhesive silicone-elastomer. Ultrasound gel is not necessary, which is a great advantage, especially in the eye area since it cannot penetrate the eye.

d. The ultrasound head is connected to the sensor, where it connects to the pressure sensor due to the adhesive properties of the coating. Again here, advantageously, no gel is necessary (see also 4.4. above).

e. The measurement is carried out by light compression on the eye via the ultrasound head, whereby simultaneously the change in diameter and the contact pressure on the eyelid is measured and correlated. In this way, an elasticity curve can be created, the gradient of which correlates with the intra-ocular pressure. A one-off measurement is also conceivable where the diameter of the eye is measured at a pre-determined pressure.

f. Intra-operative application: During operations on the eye, a rapid increase in pressure in the eye can occur, which must be detected in good time so that the doctor can take countermeasures. Intra-operative pressure monitoring of the eye is possible during the operation if the pressure sensor is placed sideways outside the operating field. Here, a holder of the pressure gauge lying on the head of the patient within the framework of the invention would be advantageous.

Other advantages, features and details of the invention result from the following description, in which exemplary embodiments of the invention are described, taking the drawings under consideration.

The reference list is an integral part of the disclosure like the technical content of the patent claims and figures are. The figures are comprehensively described in relation to one another. Identical reference numbers denote identical components, and reference characters having different indices indicate functionally identical or similar components.

Figure 3:
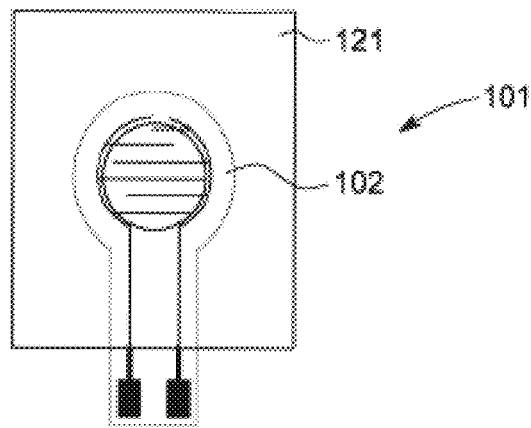
Figure 4:
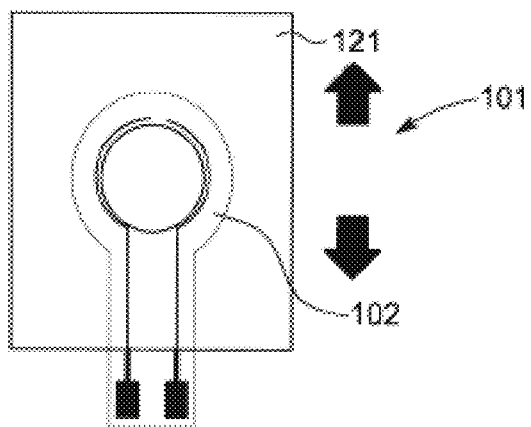
Figure 5:
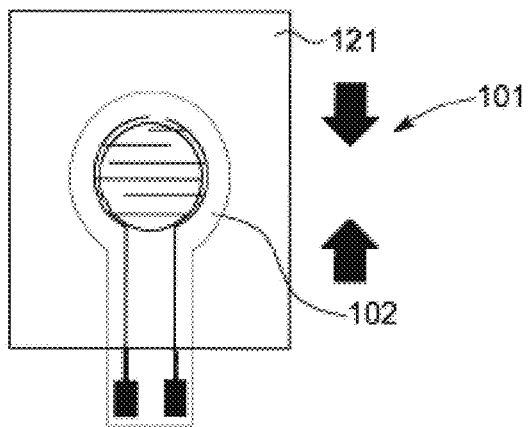
Figure 7:
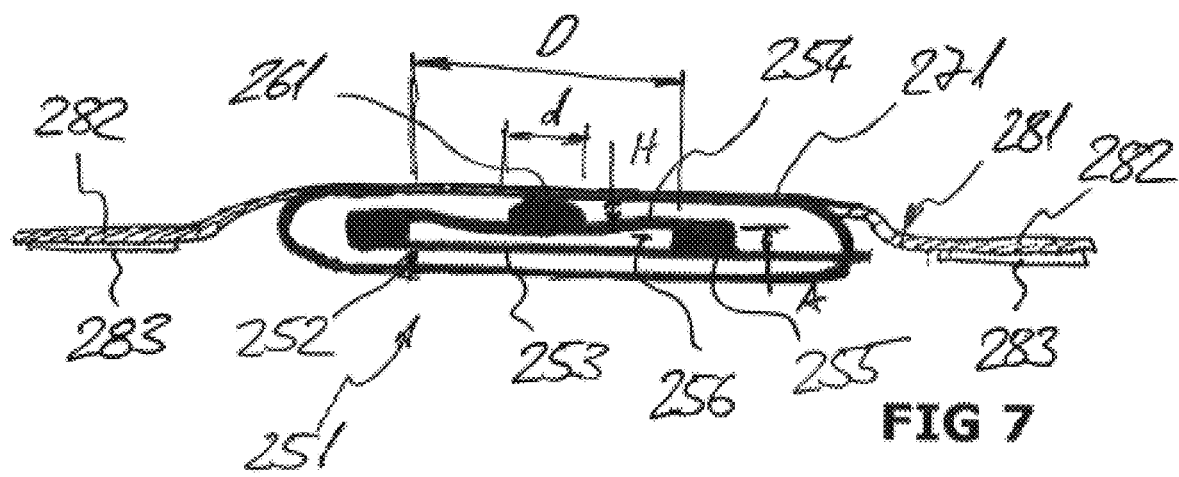

The figures shows examples of the invention:

FIG. 1 a measurement device with an inventive pressure measurement system in a schematic illustration, FIG. 2 a measuring process with the pressure measurement device according to the invention in accordance with FIG. 1, FIG. 3 an outline of a second embodiment of a pressure measurement device according to the invention in a first state, FIG. 4 the pressure measurement device in accordance with FIG. 3 in a second state, FIG. 5 like the pressure measurement device in accordance with FIG. 3 in another state, FIG. 6 a pressure measurement system according to the invention in a schematic illustration, FIG. 7 a pressure measurement device according to the invention with a holding device in a schematic sectional illustration, FIG. 8 another embodiment of a pressure measurement system according to the invention in a schematic illustration, FIG. 9 an outline of another embodiment of a pressure measurement device according to the invention, and FIG. 10 a lateral view of the pressure measurement device according to the invention according to FIG. 9.

FIG. 11 a film pressure sensor 452 according to the invention with a channel as a reservoir in exploded view FIGS. 12a and 12b adverse situations as they can occur when the transducer 446 is too wide and is lying on the edges of the film pressure sensor FIG. 13a-FIG. 13d possibilities for improving the situation according to FIGS. 12a and 12b and FIG. 14a-14d further developed film pressure sensors according to the invention each in a sectional view and in a perspective lateral view with guidance systems 449 and 549 respectively for guiding a transducer 446.

The measuring device 16 shown in FIG. 1 for pressure measurement and/or elasticity measurement of a vein, an organ or a compartment comprises a processing unit 21 and a pressure measurement system 41, which comprises an ultrasound measurement unit 46 and a pressure measurement device 51.

The processing unit 21 contains a computing unit 22 for processing the data collected by the ultrasound measurement unit 46 and by the pressure measurement device 51 as well as a display unit 23, such as a display or a touch screen, for displaying the processed or recorded data.

The data collected by the ultrasound measurement unit 46 are transmitted via a data line 47 from the ultrasound measurement unit 46 to the processing unit 21.

The data collected by the pressure measurement device 51 are transmitted via a data line 58 from the pressure measurement device 51 to the processing unit 21.

In the FIG. 2, the pressure measurement system 41 for pressure measurement of a vein 11, an organ or a compartment is shown in an enlarged illustration. The ultrasound measurement unit 46 comprises an ultrasound head that emits ultrasound and detects ultrasound reflecting back.

The contact pressure is exerted and applied onto the tissue 12, such as the skin of a person, for example on an arm, by means of a force 14 onto the ultrasonic measuring head on the ultrasound measurement unit 46. The resulting pressure or elasticity can be measured and displayed quantitatively during the study. For this purpose, the pressure measurement device 51 is provided.

The pressure measurement device 51 has a pressure sensor designed as a film pressure sensor 52. An intermediate space 56 between the films 53 and 54 of the film pressure sensor 52 is filled with an ultrasound-transparent as well as electrolytically/electrically inactive liquid.

The ultrasound-transparent and non-electrolytically active liquid is a liquid from the group of aqueous liquids, ultrasound-transparent gels, synthetic oils or biological oils. Organic oils have been shown to be particularly preferred, also synthetic oils such as Blaser Swisslube Foodoil SH 22, Item 00700-01 or Swisslube Foodoil SH32 Item 00701-01.

The filmy 53 and 54 of the film pressure sensor 52 are made of an ultrasound-transparent material. For example, the films are made of polytetrafluoroethylene, abbreviated PFTE and registered under the brand name Teflon by Dupont. An ultrasound-transparent pressure transmission element 61 is provided, which is arranged on an outer side of the film 54 of the film pressure sensor 52, which can be brought into plant with the ultrasound measurement unit 46.

The film pressure sensor 52 is arranged in a reservoir 71 for the ultrasound-transparent as well as non-electrolytically active liquid. The reservoir 71 is used to absorb the ultrasound-transparent and electrolytically/electrically inactive liquid leaking from the film pressure sensor 52 and the release of the ultrasound-transparent and electrolytically non-active liquid flowing back into the film pressure sensor 52.

An improved version dispenses with this reservoir. This saves oil and material and also allows for a smaller construction volume. In order to allow the escape and reflow of oil, a liquid channel is provided according to FIG. 11. The oil that finds its place in channel 471 corresponds approximately to the volume of the intermediate space in the film pressure sensor 452.

The pressure measurement device 101 shown in FIGS. 3 to 5 also has a film pressure sensor 102 as a pressure sensor, which is arranged in a reservoir 121 for the ultrasonic-transparent as well as non-electrolytically active liquid. A liquid connection is provided between the reservoir 121 and the intermediate space of the film pressure sensor 102.

FIG. 3 shows the film pressure sensor 102 without a measuring pressure load. The intermediate space between the film pressure sensor 102 is complete and the reservoir 121 partially filled with the ultrasound-transparent as well as electrolytic/electrically inactive liquid.

FIG. 4 shows the film pressure sensor 102 under maximum measuring pressure load. The ultrasound-transparent as well as non-electrolytically active liquid has flowed almost completely from the intermediate space of the film pressure sensor 102 into the reservoir 121.

FIG. 5 shows the film pressure sensor 102 after the measurement without a measuring pressure load. The ultrasound-transparent and non-electrolytically active liquid flows from the reservoir 121 back into the intermediate space between the film pressure sensor 102.

At the in FIG. 6 shown pressure measurement system 141 for pressure measurement of a vein 11 or an organ the pressure measurement device 151 and the ultrasound measurement unit 146 connected to a measuring unit. The pressure measurement device 151 could also be coupled with the ultrasound measurement unit 146 to a measuring unit, wherein the coupling is advantageously mechanical and further advantageously soluble formed. Mechanical coupling is easy and safe to perform for a person skilled in the art. With a detachable coupling, a used film pressure sensor 151 can be easily replaced.

At the ultrasound measurement unit 146 a transmitter 147 is provided so that the data line is replaced by a radio connection, which consists of a transmitter 147 and a receiver. The transmitter 147 is intended for the transmission of the values recorded by the ultrasound measurement unit 146 as well as by the film pressure sensor 151.

In this example, the film pressure sensor 151 is connected to the transmitter 147 via a data line 158. In an alternative embodiment (not shown here), the film pressure sensor 151 can have a transmitter for transmitting data.

The design of the transmission path can take place in a way that is known from prior art. It can be one-way or bidirectional. If necessary, the Bluetooth® or Zigbee® standard can be used as the basis for the wireless connection.

Furthermore, it is possible to receive the data supplied by transmitter 147 several times by means of a plurality of receivers and to process them in an appropriate manner. For example, pressure measurement series can be saved to determine systematic measurement errors. In addition, different measurement data sets can be compared for training purposes.

The above data acquisition is applicable for all types of pressure measurement systems according to the invention.

In the pressure measurement device 251 according to FIG. 7, the film pressure sensor 252 is also arranged in a reservoir 271. The film pressure sensor 252 has a film 253 and a film 254, which are spaced away from one another by a spacer 255. The spacer 255 as well as the films 253 and 254 enclose the intermediate space 256 filled with an ultrasound-transparent and electrolytically/electrically inactive liquid.

The film 253 is electrically printed on the inside side, i.e. on the side facing the other film 254. The other film 254 has an electric contact grid on the inside side, i.e. on the side facing the first film 253, which was applied by means of printing. Due to the spacer 255, the two films 253 and 254 are kept at a distance from each other and direct contact of the printed film sections is prevented. When pressed on the film pressure sensor 251, the printed sides of films 253 and 254 come into contact and form electrical bridges depending on the pressure applied. The measurable electrical resistance thereby changes, and the magnitude of the applied pressure can be determined by means of the same.

On the outside, i.e. on the side facing away from the first film 253, the film 254 is provided with an ultrasound-transparent pressure transmission element 261. The pressure transmission element 261 has in this exemplary embodiment an elevation extension H, which corresponds at least to the distance A of the films 253 and 254 of the film pressure sensor 251. In this exemplary embodiment, the pressure transmission element 261 has a circular extension with a diameter d, which corresponds to about 40% to 60% of the corresponding extent D of the intermediate space 256 of the film pressure sensor 251.

Furthermore, a holding device 281 is provided, by means of which the pressure measurement device 251 is temporarily fixed on a tissue. The holding device comprises beyond the extension of the reservoir 271 protruding retaining portions 282, which are provided on one side with an adhesive layer 283. As an adhesive for the adhesive layer 283, an adhesive is advantageously used, as it is also used for plasters.

This plaster-like holding device is applicable to all pressure measurement systems according to the invention. Alternatively, it can also be replaced by a self-adhesive silicone-elastomer, with which the film pressure sensor can be glued to the skin and/or to the transducer.

On this occasion it is mentioned that with the pressure measurement device according to the invention also objects (not only humans or animals) can be measured, provided their cavities behave similarly to those in an animal or human body.

An inventive film pressure sensor with one- or two-sided coating with adhesive silicone-elastomer represents an independent invention. This own invention is optionally further developed in that the silicone-elastomer is adjusted with respect to its adhesive properties so that it has higher cohesion values/cohesion forces than adhesion values/cohesion forces. Therefore, it can be removed without residue.

The pressure measurement device 351 shown in FIGS. 9 and 10 also has a film pressure sensor 352, which in the structure essentially corresponds to the aforementioned film pressure sensors 52, 102 or 252. The embodiments made in connection with these film pressure sensors 52, 102 or 252 apply analogously.

The film pressure sensor 352 is embedded in an ultrasound-transparent embedding material 358. The embedding material 358 is, for example, an ultrasound-transparent silicone, which is already commercially available. For example, the silicone with the product name Köraform A 42 made by Bezema AG from Switzerland is used. The silicone can be poured into any shape.

The film sensor 352 is—as shown in FIGS. 8 to 10—completely embedded in the embedding material 358.

In an alternative embodiment not shown in the figures, the film sensor 352 can also be embedded only in the embedding material 358 in sections. In another alternative embodiment not shown in the figures, the film sensor 352 can also be arranged on a block of an ultrasound-transparent material, for example glued.

The embedding material casting is preferably round or adapted to the embodiment of the used film pressure sensor. The dimensions of the embedding material are chosen in such a way that an ultrasonic window large enough for use is created, which still allows to map the structures to be measured in the ultrasound image.

The thickness of the embedding material 358 is advantageously thinly formed in such a way that the influence of the same on the ultrasound measurement is as low as possible. In the tests carried out, a thickness in a range of 2 mm to 15 mm, preferably in a range of 3 mm to 10 mm, has been shown to be particularly advantageous.

A pressure transmission element 361 is provided on the outer side of the film pressure sensor 352 or the pressure measurement device 351, which can be brought to rest on the skin or the tissue 12.

The pressure transmission element 361 is used for the power transfer from the flexible skin or tissue 12 to the film pressure sensor 352. Advantageously, the pressure transmission element 361 is arranged in the centre of the film pressure sensor 352.

The pressure transmission element 361 has an extension d, which corresponds to approximately 30% to 70% of the corresponding extent D of the intermediate space 356 of the film pressure sensor 352. The pressure transmission element 361 further has an elevation extension H, which corresponds about 5 times to 20 times the distance of the films 353, 354 of the film pressure sensor 352 to each other.

The extension D of the intermediate space 356 of the film pressure sensor 352 is smaller than the electrically active measuring surface of the film pressure sensor 352.

For example, the 352 film pressure sensor is a force sensing resistor (FSR) by Interlinks Electronics, such as FSR 402 long, which has an active measuring surface of 22 mm$^2$. When using this type of film pressure sensor 352, a height extension in the range of 0.5 mm to 3 mm has been shown to be advantageous in experiments.

Furthermore, a reservoir 371 is provided for the ultrasound-transparent as well as electrolytic/electrically inactive liquid. A liquid connection is provided between the reservoir 371 and the intermediate space 356 of the film pressure sensor 352, for example, in the form of a channel or a line section.

The liquid connection ensures that when using the pressure measurement device 351, the ultrasound-transparent and non-electrolytically active liquid from the intermediate space 356 in the film pressure sensor 352 can leak and re-enter without disturbing air mixing, which would impair the ultrasonic conductivity of the liquid and thus the imaging.

Favourably, an advantageously sealable filling opening 372 is provided, via which, as required, the ultrasound-transparent as well as electrolytically/electrically inactive liquid can be supplied or discharged.

At the in FIG. 8 shown pressure measurement system 341 for pressure measurement of a vein 11 or an organ the pressure measurement device 351 and the ultrasound measurement unit 346 connected to a measuring unit.

For coupling the pressure measurement device 351 with the ultrasound measurement unit 346, an adapter 349 is provided, which is L-shaped in this exemplary embodiment. Other possible embodiments of the adapter represent—not exhaustively—flat or U-shaped formations. The adapter 349 serves as a connection piece to the ultrasound head 346. The adapter 349 secures the position of the pressure measurement device 351 in front of the ultrasound head 346 so that the pressure to be applied can be transferred to the pressure measurement device 351.

The adapter 349 can be made of an embedding material 358, for example from a silicone. Advantageously, the same embedding material 358 is used, which is provided for embedding the film sensor 352. This can be used to save a plurality of work steps in the production of the pressure measurement system 341.

Preferably, this embedding material has Shore hardness 30. Further preferred, the embedding material is also self-adhesive.

A data line 348 is intended for passing on the values determined by the film pressure sensor 352.

In the gaps between the ultrasound head 346 and the embedding material 358 as well as between the pressure measurement device 351 and the skin or tissue 12, an ultrasound-transparent gel or an ultrasound-transparent liquid, e.g. a commercially approved for use ultrasound gel, is advantageously provided.

This gel can be dispensed with if the embedding material in accordance with a further embodiment of the invention is self-adhesive silicone-elastomer so that both the skin as well as the transducer are connected to each other via bonding.

In particular, with the pressure measurement devices 51, 101, 151, 251 or 351 venous pressures and organ pressures can be determined and elasticity measurements of organs and tissues in particular of compartments can be carried out. This allows, for example, a fast and cost-effective, non-invasive measurement of peripheral and central venous pressure (ZVD). Furthermore, this enables a cost-effective, non-invasive measurement of elasticity in a muscle compartment to assess the pressure within the compartment (so-called compartment syndrome). The previous conventional measurement of the ZVD is carried out invasively by inserting a catheter into the upper hollow vein. Such a measurement has a complication rate of approximately 20% and is associated with partially serious risks for patients. In addition, the insertion of the catheter takes about 23 minutes and must be carried out by two persons, one of whom must be a doctor. The procedure is relatively expensive. In contrast, the pressure measurement system 41, 141 or 341 according to the invention provides a non-invasive faster, simpler, cheaper and complication-free measuring method for venous pressure measurement.

The pressure measurement and/or elasticity measurement can be carried out by means of the inventive system here by trained personnel or semi-skilled investigators.

The use of the pressure measurement system 41, 141 and 341 according to the invention leads to faster operations and allows a largely automated measurement of the central venous pressure, similar to that of conventional blood pressure monitors for arterial blood pressure. For this purpose, a combination of an ultrasonic measurement head 46, 146 or 346 and a pressure measurement device 51, 101, 151, 251 or 351 on patient tissue to be examined, for example, placed on the arm of a patient and measured via the pressure measurement device 51, 101, 151, 251 or 351, as shown in the above exemplary embodiments, the pressure resulting from the applied force in the tissue 12. Simultaneously, ultrasound is used to observe how a vein 11 located in the tissue 12 behaves. As soon as, for example, the vein 11 collapses, the associated pressure in tissue 12 can be determined, which then corresponds to the pressure of the blood in the vein 11.

In an elasticity measurement of a vein 11, an organ or a compartment, the elasticity resulting from the applied force in tissue 12 is measured and an elasticity quotient is determined from it. The determined elasticity quotient is then correlated with organ pressure.

Of course, the measurement method is not limited to pressure measurements and/or elasticity measurement of veins, but can also be applied to other tissue structures, in particular organs or organ parts (e.g. the liver or spleen, muscle tissue and muscle compartments) and compartments of the body and other body fluids.

The aforementioned devices can be used for the non-invasive measurement of intracranial pressure in new-borns with a fontanelle that is still open.

Advantageously, the measurement process can be started automatically. As soon as a pressure pulse from the film pressure sensor 52, 102, 152, 252 or 352 is measured, for example, how the processing device 21 can be switched on, further, the ultrasound measurement unit 46, 146 or 346 can be started via a suitable signal. An automatic start-up process has the advantage that the pressure measurement system 41, 141 or 341 according to the invention can be used in an energy-efficient manner. It is also conceivable that by appropriate analytical methods it is possible to automatically determine the point in time at which a vein 11 or another body fluid vessel collapses. For example, it is conceivable that the change in a blood flow noise is used via a structure-borne sound microphone as an indicator for the collapse of a vein 11.

It is also conceivable to automatically analyse images from the inside of the tissue 12 in an extremity (e.g. in an arm) by image-processing methods in order to detect the position of a vein 11 and determine its geometry change.

In this way, a detection of the collating of the vein 11 can also be carried out to determine the point in time of correct measurement of the venous pressure. This time is then determined in the course of the pressure measurement as the point in time at which the central venous pressure was determined.

Further, advantageously on a display unit 23 simultaneously to the pressure course an image of the by ultrasound observed vein 11 be represented side by side or on top of each other. Such an embodiment offers the advantage of a compact display and only allows for having to provide one display device 23 for a plurality of display functions.

In further embodiments, it is conceivable, for example, to collect the measurement values measured by the pressure measurement device according to the invention and to use them for quality control, in particular, to be able to understand the correct position of the pressure determination, that is, the correct position over a vein 11, and to be able to understand whether the correct and sufficient force for the pressure measurement or the elasticity measurement was exerted on the tissue 12.

Generally, automated methods in embodiments of the pressure measurement device 16 according to the invention and the inventive pressure measurement system 41, 141 and 341 have the advantage that fewer errors occur. It is also conceivable to use the method for measuring liver stiffness. For this purpose, the liver is deformed by means of the increasing pressure in the measuring fluid up to a certain degree of deformation, wherein the ratio of degree of deformation to pressure represents the measure for liver stiffness. Alternatively, the liver stiffness can also be measured by determining the pressure of a liver vein and, conversely, it is determined that the higher the pressure in the liver vein is, the stiffer the liver tissue is.

The following describes possible user errors in venous pressure measurement and measures against it.

The arrangement of the pressure measurement device is too far away from the axis with respect to the target vein and therefore no peak pressure is applied to the vein. Therefore, preferably, the method of the invention for venous pressure measurement should perform a detection of the centre axis of the pressure measurement system and a comparison of the same with the target vein. Preferably, the target vein is marked in colour on the display unit.

If the pressure measurement device is not in an ideal position for an accurate pressure measurement, preferably, a warning of the investigator is given with a request to correct the position of the pressure measurement device and no release of the pressure measurement is carried out.

The exertion of pressure by the pressure measurement device on the vein is uneven and leads to the asymmetric tissue shift between the pressure measurement device, which comes into contact with the tissue 12 and the vein 11. Therefore, according to the invention, surface displacement methods and elastographic methods are used to detect such cases.

Preferably, in such a case, a warning of the investigator is made with request for correction with request for uniform pressure application and no release of the pressure measurement is made.

And arrangement of the pressure measurement device takes place in an unsuitable location. As a remedy, an evaluation of the contact area for the pressure measurement device is provided according to the invention.

For example, a suitable location for venous pressure measurement is found by searching for internal bone below the target vein 11. Preferably, an investigator warning is made with request to correct the placement of the pressure measurement device and no release of the pressure measurement takes place.

advantageously, a visible display of the measuring cycle is also provided. This can be used to automatically detect the point in time at which the measurement was started by evaluating the vein geometry and its deformation (for example, the beginning of the measurement at 5% geometry change from vein height to vein width).

Furthermore, a notification of the investigator can preferably be made about the fact that the measurement has begun. For example, this can be done by changing the colours of certain areas of the screen or display unit 23.

Advantageously, it is ensured that the investigator knows that a measuring cycle has been started, and furthermore, a further date is made available to the investigator for evaluation in the form of the initial pressure at the first movement of the vein geometry.

A visible display of the end of the measurement cycle is also provided. This allows an automatic detection of the point in time at which the vein 11 collapsed and the measurement was completed by evaluating the vein geometry and its deformation. For example, "Complete" can preferably be defined if 95% of the geometry change from vein height to vein width is present, or as soon as no hollow area in the vein 11 can be detected.

Preferably, the investigator is notified of the fact that the measurement has been completed. This is done, for example, by changing the colours of certain areas on the screen and by displaying the measurement result in, advantageously large, digits on the display unit (screen). Advantageously, this ensures that the investigator knows that a measurement cycle has ended. This data can be used, and a new measurement can also be started.

Preferably, according to the invention, it can be ensured that the continuation of the measurement is carried out by further data collection at the same position. Therefore, an automatic detection of further measurements is preferably carried out, which allows the investigator to carry out a further measurement after a poor measurement taking into account the above-mentioned criteria. When the measurement cycle is complete, the new measurement is also displayed. Preferably, an average with the preceding measurements at the same location is also displayed with the value of the preceding measurement.

Continuous monitoring of the pressure and the analysed image results advantageously in an automatic detection of the measuring end. As soon as, for example, the investigator lifts the pressure measurement device from the patient's skin or moves it too far from the starting point of the measurement, the measurement can be advantageously terminated. In cases, a new measuring cycle can be initiated advantageously, as soon as the investigator presses the actuating button on the pressure measurement device or the pressure measurement device comes into contact with the skin and the pressure increases, wherein advantageous tissue 12 can be detected by an evaluation software.

For example, such an option can be selected from a personal setting menu within the software.

In order not to confuse the investigator and for the purpose of a clear presentation, the measured and evaluated data are advantageously displayed in a combined frame together with the ultrasound image, which is delivered by the medical ultrasound device.

In order to give an investigator up-to-date information on the quality of the measurement cycle, the detected typologies of skin, surface of the venous pressure device, vein, bone; displayed on the screen as explained above and coloured according to their status. For example, topology means green "no problem", red "unacceptable" and orange "critical".

The method according to the invention for pressure measurement and/or elasticity measurement of a vein or an organ specifies a simple procedure, whereby a pressure measurement device consisting of pressure measurement device and ultrasound measurement unit can be used for the automated measurement of venous and or organ pressures or of vein and or organ elasticities.

For the skilled person skilled in the art, in view of the above description and exemplary embodiments of the pressure measurement device according to the invention, the pressure measurement system and the method pressure measurement and/or elasticity measurement of a vein or an organ variations within the scope of the technical possibilities and the known devices for pressure and ultrasound measurements are conceivable.

REFERENCE LIST 11 vein
12 tissue
14 force (arrow)

16 measurement device
21 processing unit
22 computing unit
23 display unit
41 pressure measurement system
46 ultrasound measurement unit
47 data line
51 pressure measurement device
52 film pressure sensor
53 (lower) film
54 (upper) film
56 intermediate space
58 data line
61 pressure transmission element
71 reservoir
101 pressure measurement device
102 film pressure sensor
121 reservoir
141 pressure measurement system
146 ultrasound measurement unit
147 transmitter
151 pressure measurement device
158 data line
251 pressure measurement device
252 film pressure sensor
253 (lower) film
254 (upper) film
255 spacer
256 intermediate space
261 pressure transmission element
271 reservoir
281 holding device
282 retaining portion
283 adhesive layer
H Height extension of 261 or 361
A Distance between films (253/254)
d Diameter of 261 or 361
D Extension of 256 or 356
341 pressure measurement system
346 ultrasound measurement unit
348 data line
349 adapter
351 pressure measurement device
352 film pressure sensor
353 (lower) film
354 (upper) film
356 intermediate space
358 embedding material
361 pressure transmission element
371 reservoir
372 fill opening
449 adapter
451 pressure measurement device
452 film pressure sensor
453 (lower) film
454 (upper) film
456 intermediate space
461 pressure transmission element
471 channel, which is used for filling on the one hand and as a reservoir on the other
549 adapter/target
551 pressure measurement device
552 film pressure sensor
553 (lower) film
554 (upper) film
556 intermediate space
561 pressure transmission element
571 channel, which is used for filling on the one hand and as a reservoir on the other
651 pressure measurement device
652 film pressure sensor
653 (lower) film
654 (upper) film
656 intermediate space
671 channel, which is used for filling on the one hand and as a reservoir on the other
751 pressure measurement device
752 film pressure sensor
753 (lower) film
754 (upper) film
756 intermediate space

The invention claimed is:

1. A pressure measurement device for measuring pressure and/or for measuring elasticity of a vein, an organ or a compartment and for combination with an ultrasound measurement unit,
wherein a pressure sensor, configured as a film pressure sensor, is provided,
an intermediate space between films of the film pressure sensor is filled with an ultrasound-transparent and electrolytically/electrically inactive liquid, and
the films of the film pressure sensor are fabricated from an ultrasound-transparent material, at least in some regions of said material.

2. The pressure measurement device according to claim 1, wherein the ultrasound-transparent and electrolytically/electrically inactive liquid is a liquid selected from the group consisting of aqueous liquids, ultrasound-transparent gels, synthetic oils or biological oils.

3. The pressure measurement device according to claim 1, wherein the ultrasound-transparent oil is either:
a synthetic oil with a density of about 0.83 g/cm$^3$ (DIN 51757/ASTM D1217) and/or a viscosity kinematic at 40° C. of about 32 mm$^2$/s (ISO 3104/ASTM D445), or
an olive oil, or
a rape seed oil.

4. The pressure measurement device according to claim 1, wherein at least one pressure transmission element is provided on at least one of the films, or
the at least one of the films is configured to be raised or cambered.

5. The pressure measurement device according to claim 4, wherein the at least one pressure transmission element is arranged on an outer side of the film pressure sensor or the pressure measurement device, which can be brought to abut with the ultrasound measurement unit, and
the pressure transmission element has a height extension (H) which at least corresponds to a spacing (A) of the films of the film pressure sensor, and has a surface extension (d) which corresponds to approximately 30% to 70% of the corresponding surface extension (D) of the intermediate space of the film pressure sensor.

6. The pressure measurement device according to claim 4, wherein the at least one pressure transmission element is arranged on an outer side of the film pressure sensor or the pressure measurement device which can be brought to abut with skin or tissue,
the at least one pressure transmission element has an extension (d) which corresponds to approximately 30% to 70% of the corresponding extension of the film pressure sensor and has a height extension (H) which corresponds to approximately 5% to 20% of the corresponding extension (D) of the intermediate space of the film pressure sensor.

7. The pressure measurement device according to claim 1 wherein a reservoir is provided for the ultrasound-transparent and electrolytically/electrically inactive liquid, that subsequently delivers the ultrasound-transparent and electrolytically/electrically inactive liquid into the intermediate space of the film pressure sensor, as required, and can transfer the ultrasound-transparent and electrolytically/electrically inactive liquid from there.

8. The pressure measurement device according to claim 7, wherein, between the reservoir and the intermediate space of the film pressure sensor, a liquid connection is provided, and the film pressure sensor is arranged in an interior of the reservoir.

9. The pressure measurement device according to claim 7, wherein the reservoir is configured as a laterally projecting channel, whose volume approximately corresponds to a volume of the intermediate space of the film pressure sensor, which, in a rest state however, is not completely filled and a closure opens when the sensor is released from a packaging.

10. The pressure measurement device according to claim 7, wherein a data line is provided for relaying values determined by the film pressure sensor or a transmitter is provided for relaying the values determined by the film pressure sensor, and the data line extends parallel to a channel.

11. The pressure measurement device according to claim 1, wherein a holding device is provided for the pressure measurement device, which can be fixed temporarily on a tissue and/or the holding device and/or the pressure measurement device is fixed to a plaster-like or band-aid-like carrier.

12. The pressure measurement device according to claim 1, wherein the film pressure sensor, at least in some regions, is embedded in an ultrasound-transparent embedding material, the embedding of the film pressure sensor is provided at least on an outer side of the film pressure sensor which can be brought to abut with skin or tissue, and the embedding material has at least one haptic formation which acts as a guidance system for a transducer so that the film pressure sensor can be readily placed at the location to be measured and the transducer can be placed on the film pressure sensor in a readily guided manner.

13. A pressure measurement system for measuring the pressure and/or the measuring elasticity of the vein, the organ, or the compartment at least comprising a pressure measurement device according to claim 1 and an ultrasound measurement unit, wherein the pressure measurement device and the ultrasound measurement unit are coupled to one another, advantageously mechanically or via adhesive force, into a measurement unit or are connected together into a measurement unit.

14. The measurement device for measuring the pressure and/or the measuring elasticity of the vein, the organ or the compartment at least comprising a processing unit and a pressure measurement system which comprises an ultrasound measurement unit and the pressure measurement device according to claim 1.

15. The pressure measurement device according to claim 1, wherein at least one pressure transmission element is provided on at least one of the films, or the upper film is configured to be raised or cambered.

16. The pressure measurement device according to claim 7, wherein the reservoir is configured as a laterally projecting channel, whose volume approximately corresponds to a volume of the intermediate space of the film pressure sensor, which, in a rest state however, is not completely filled and a closure automatically opens when the sensor is released from a packaging.

17. The pressure measurement device according to claim 1, wherein the films of the film pressure sensor comprise two films which are opposed to each other across the intermediate space that is filled with the ultrasound-transparent and the electrolytically/electrically inactive liquid, the film pressure sensor detecting a magnitude of pressure depending on a change in an area of contact of the two films when a pressure is applied on the film pressure sensor.

* * * * *